US011835502B2

(12) United States Patent
Gho et al.

(10) Patent No.: US 11,835,502 B2
(45) Date of Patent: Dec. 5, 2023

(54) ANALYSIS METHOD FOR EXTRACELLULAR VESICLES, USING SIZE EXCLUSION CHROMATOGRAPHY, AND USE FOR SAME

(71) Applicants: ROSETTA EXOSOME, Seoul (KR); POSTECH ACADEMY-INDUSTRY FOUNDATION, Pohang-si (KR)

(72) Inventors: Yong Song Gho, Gyeongsangbuk-do (KR); Chang Jin Lee, Daegu (KR); Hyun Taek Park, Gyeongsangbuk-do (KR)

(73) Assignee: ROSETTA EXOSOME, Seoul (KR)

( * ) Notice: Subject to any disclaimer, the term of this patent is extended or adjusted under 35 U.S.C. 154(b) by 640 days.

(21) Appl. No.: 16/651,940

(22) PCT Filed: Sep. 27, 2018

(86) PCT No.: PCT/KR2018/011443
§ 371 (c)(1),
(2) Date: Mar. 27, 2020

(87) PCT Pub. No.: WO2019/066501
PCT Pub. Date: Apr. 4, 2019

(65) Prior Publication Data
US 2020/0284770 A1 Sep. 10, 2020

(30) Foreign Application Priority Data

Sep. 27, 2017 (KR) .................. 10-2017-0124856
Sep. 27, 2018 (KR) .................. 10-2018-0115206

(51) Int. Cl.
| | | |
|---|---|---|
| G01N 21/64 | (2006.01) | |
| G01N 33/50 | (2006.01) | |
| G01N 30/88 | (2006.01) | |
| C12Q 1/6804 | (2018.01) | |
| C12Q 1/6837 | (2018.01) | |

(52) U.S. Cl.
CPC ........... *G01N 30/88* (2013.01); *C12Q 1/6804* (2013.01); *C12Q 1/6837* (2013.01); *G01N 21/64* (2013.01); *G01N 33/5076* (2013.01)

(58) Field of Classification Search
CPC ................................ B01D 15/34; G01N 30/02
See application file for complete search history.

(56) References Cited

U.S. PATENT DOCUMENTS

| | | |
|---|---|---|
| 2014/0186264 A1 | 7/2014 | Taylor et al. |
| 2015/0301058 A1 | 10/2015 | Schettini et al. |

FOREIGN PATENT DOCUMENTS

| | | |
|---|---|---|
| KR | 10-2010-0127768 A | 12/2010 |
| KR | 10-2010-0127768 A | 12/2010 |
| WO | WO 2011/066589 A1 | 6/2011 |
| WO | WO 2012/006476 A2 | 1/2012 |

OTHER PUBLICATIONS

Gamez-Valero, A. et al., Size-Exclusion Chromatography-based Isolation minimally alters Extracellular Vesicles' characteristics compared to precipitating agents, Scientific Reports, vol. 6:33641, pp. 1-9 (Year: 2016).*
Aizea Morales-Kastresana, et al., "Labeling Extracellular Vesicles for Nanoscale Flow Cytometry", Scientific Reports, www.nature.com/scientificreports; May 12, 2017, pp. 1-10.
Written Opinion of the International Searching Authority corresponding to International application No. PCT/KR2018/011443 dated Feb. 11, 2019.
International Search Report corresponding to International application No. PCT/KR2018/011443 dated Feb. 11, 2019.

* cited by examiner

*Primary Examiner* — Teresa E Strzelecka
(74) *Attorney, Agent, or Firm* — Carter, DeLuca & Farrell LLP; George Likourezos

(57) ABSTRACT

The analysis method for extracellular vesicles, according to the present invention, uses the size-specific separation ability of size exclusion chromatography and the properties of a probe that specifically binds with extracellular vesicles, and by using same is capable of the rapid and easy analysis of the quantity of extracellular vesicles included in a sample, analysis of the physicochemical properties of the extracellular vesicles, analysis of the kind and quantity of the components included in the extracellular vesicles, and analysis of the binding properties or affinity of the probe with respect to the components of the extracellular vesicles. In addition, using the analysis method of the present invention not only enables accurate analysis of extracellular vesicles in a sample, without a sample purification or pre-processing step, but also enables accurate and simple analysis of the components of extracellular vesicles, according to the kind of probe, and thus can improve the efficiency of diagnosis using extracellular vesicles. Also, analysis of the properties or affinity of the probe can be applied to, for example, extracellular vesicle-specific antibody screening, protein screening and chemical-substance screening.

19 Claims, 26 Drawing Sheets

FIG. 2
(a)
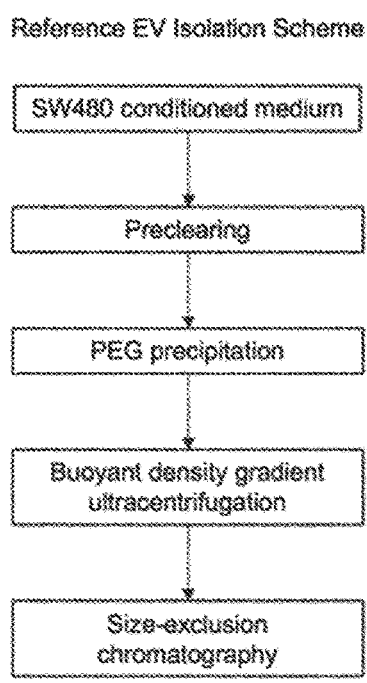
(b)
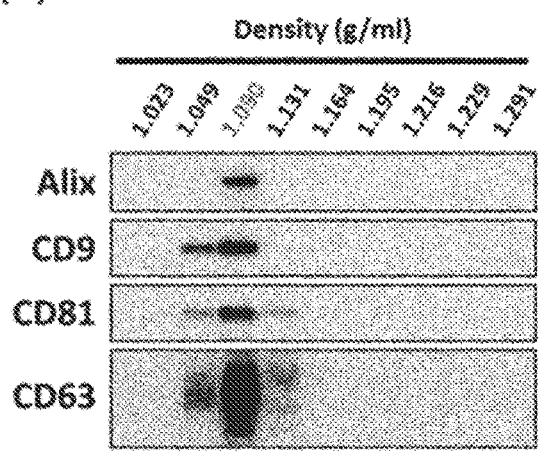
(c)
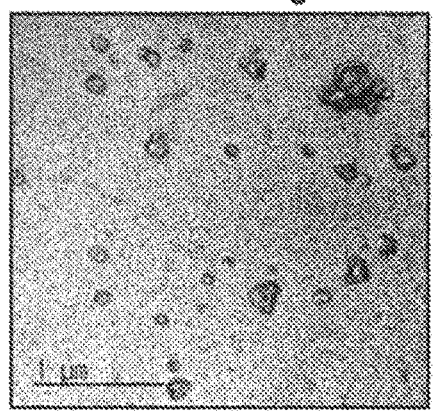

FIG. 5
(a) 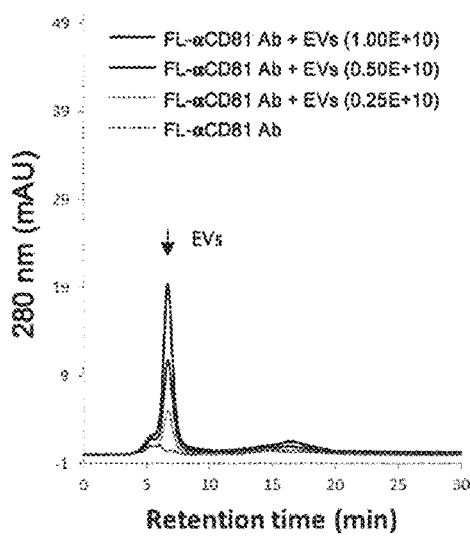
(b) 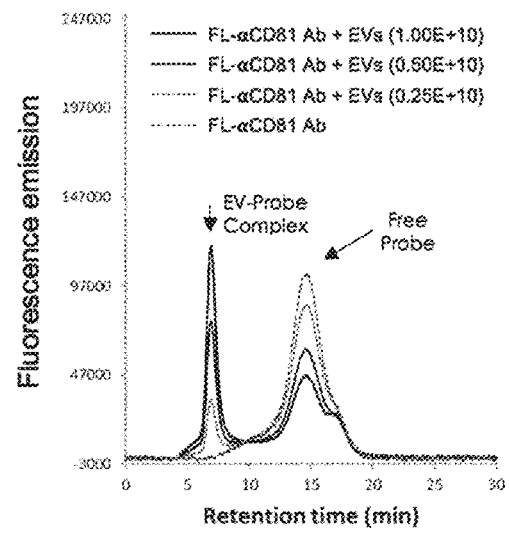

FIG. 7
(a) 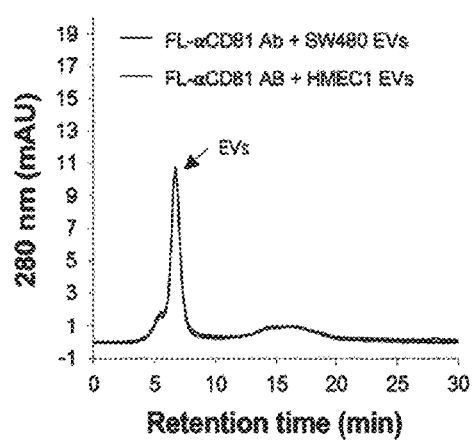
(b) 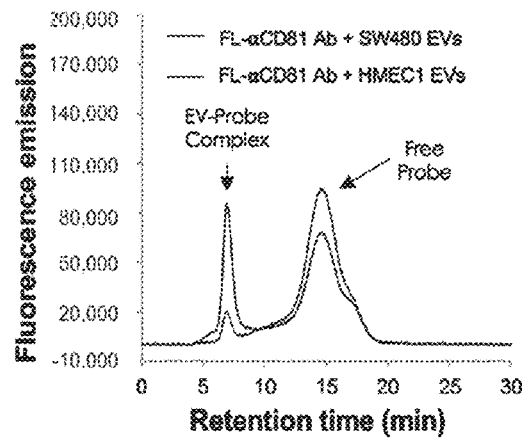

FIG. 10
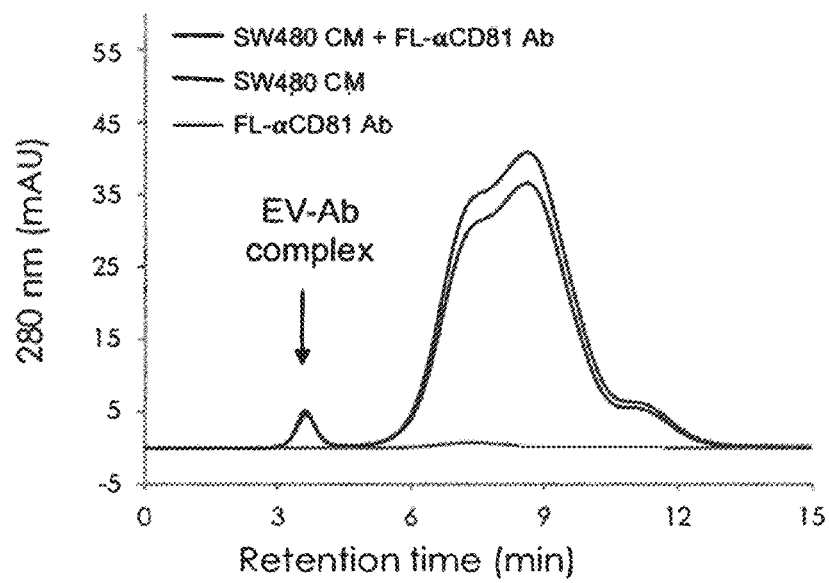
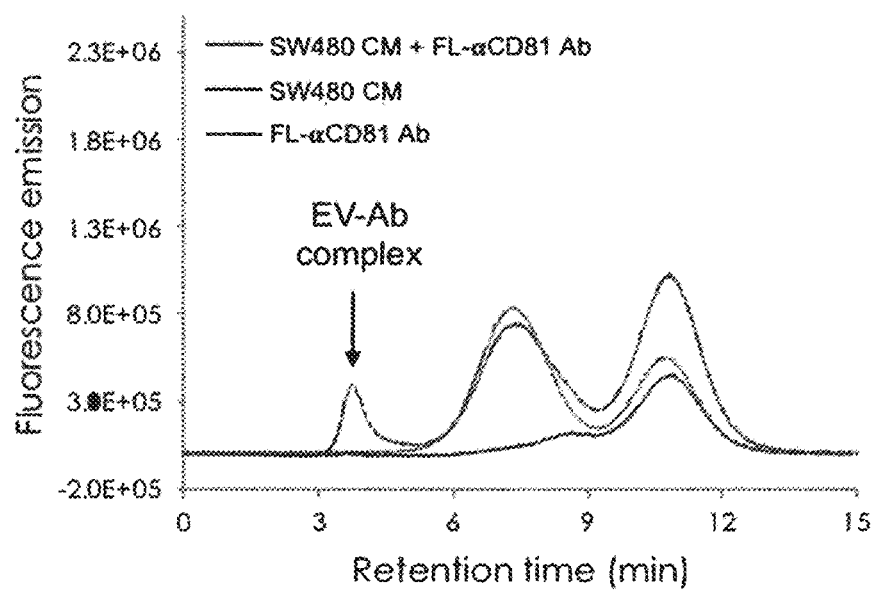

FIG. 12
(a)
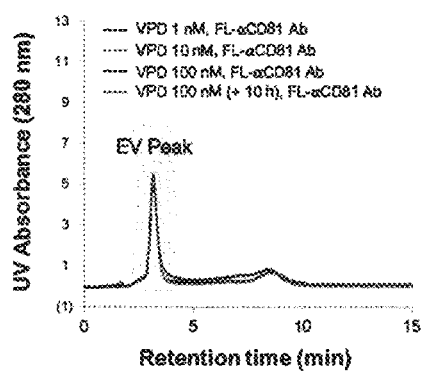
(b)
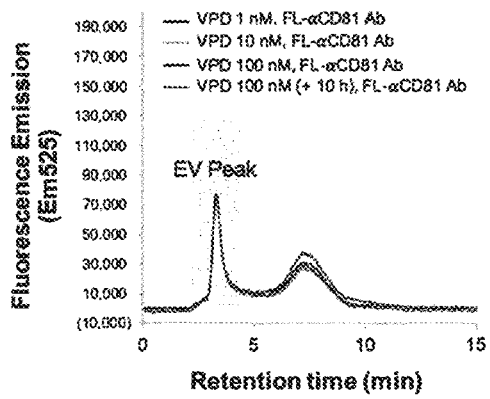
(c)
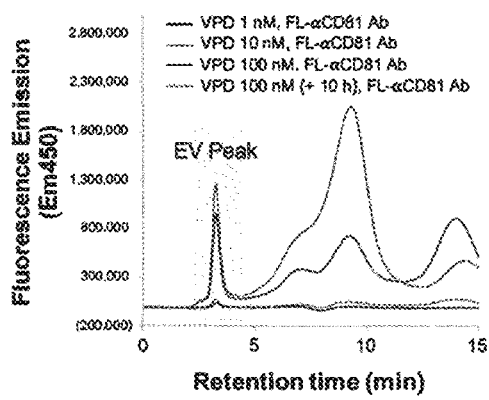

FIG. 13
(a)
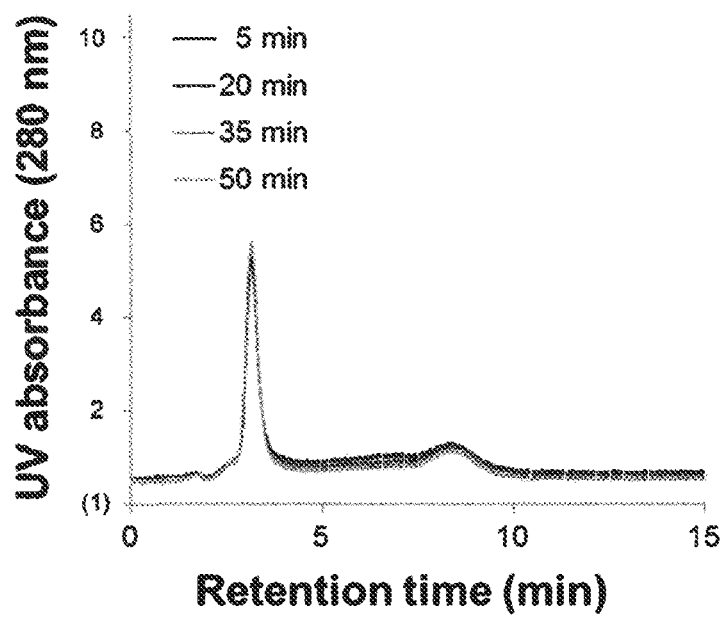
(b)
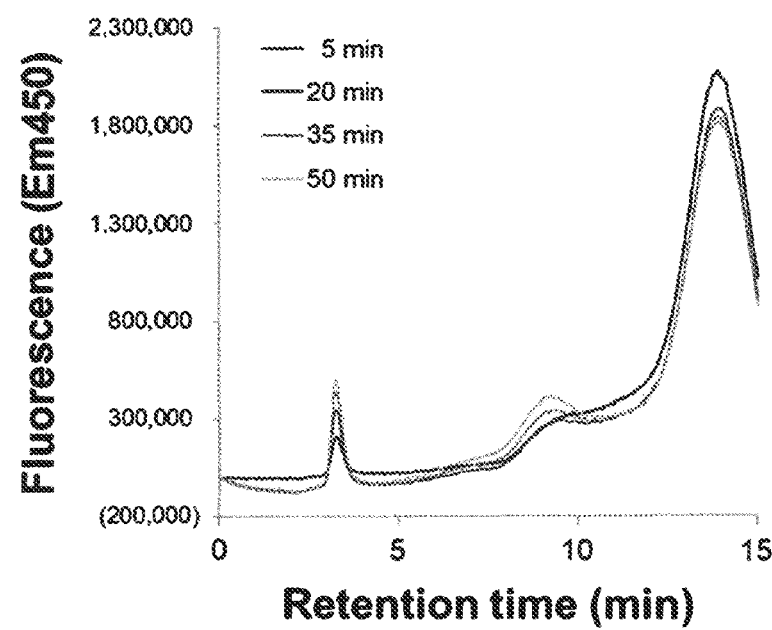

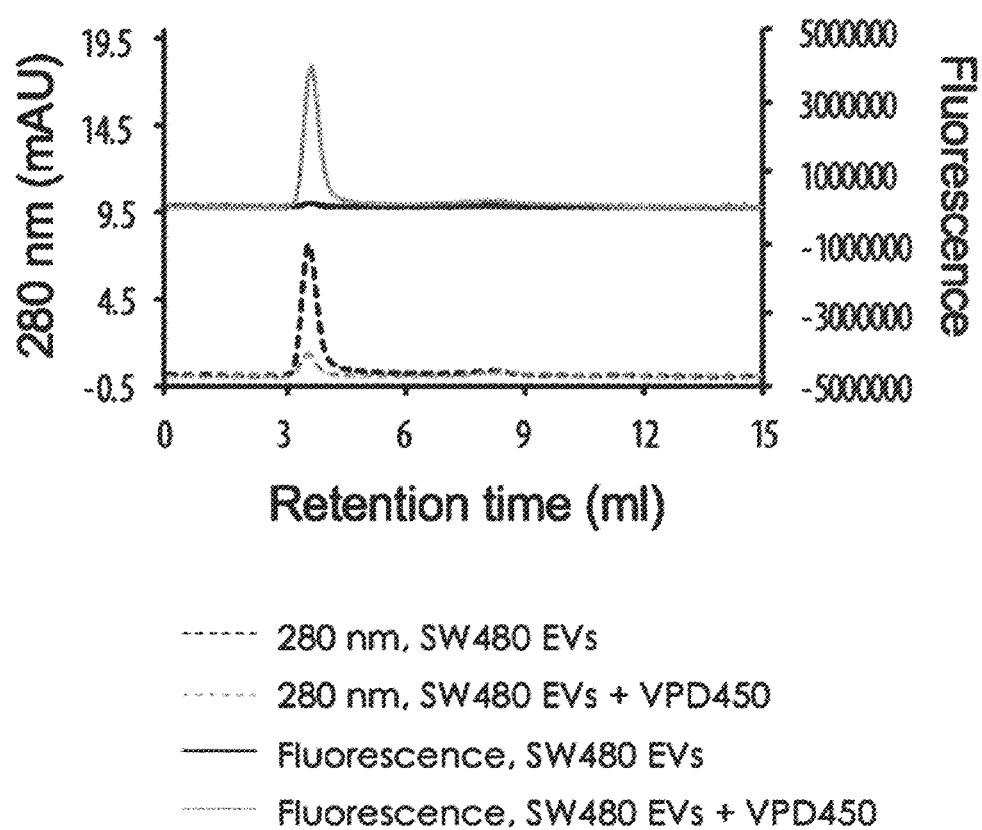

FIG. 15A
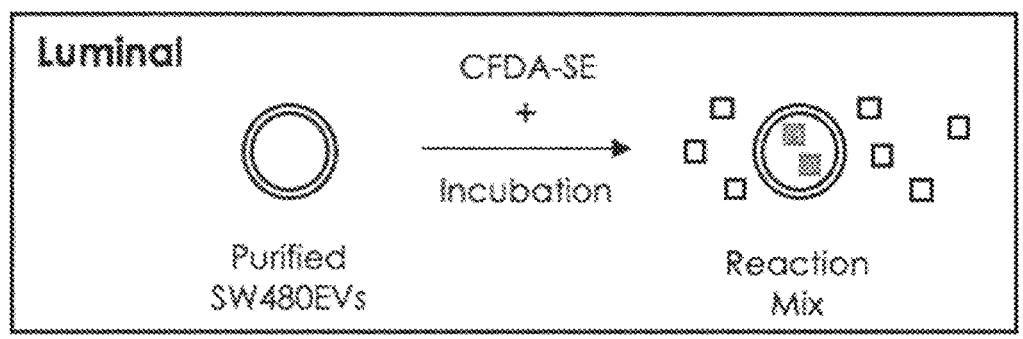
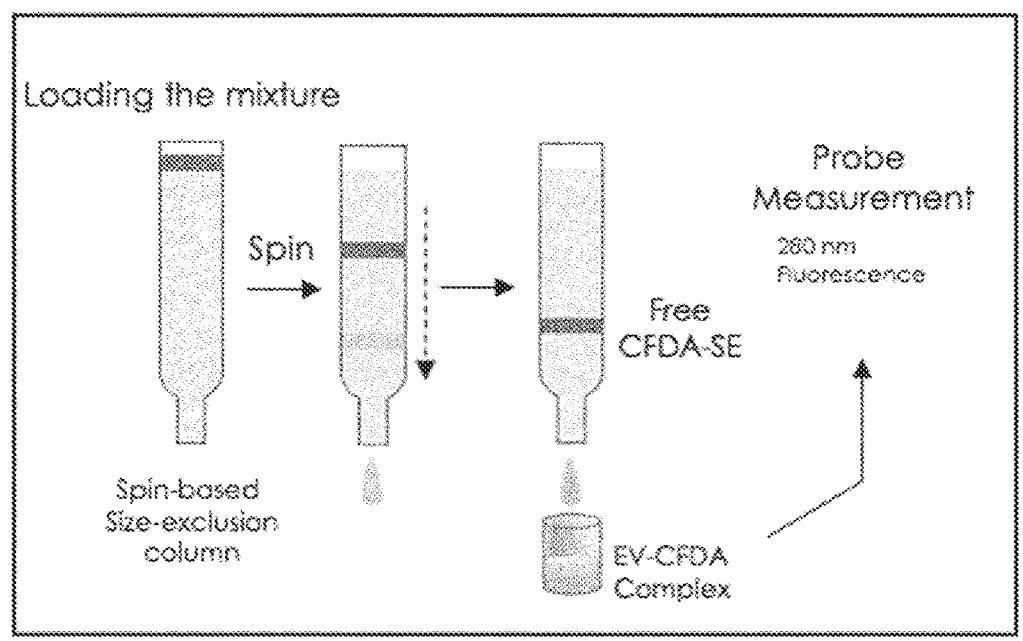

FIG. 16A
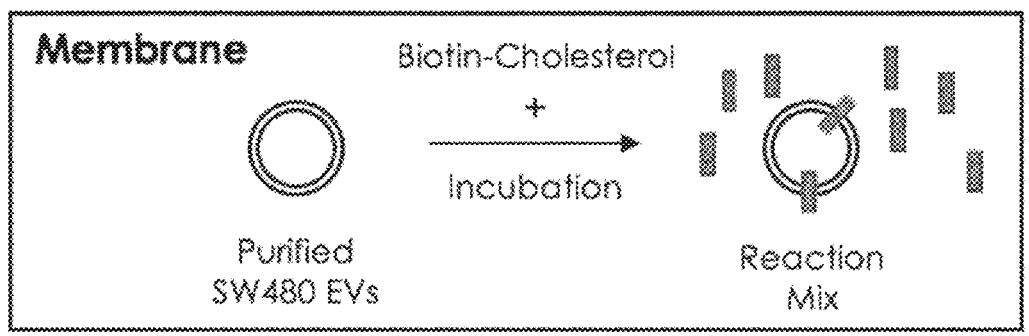
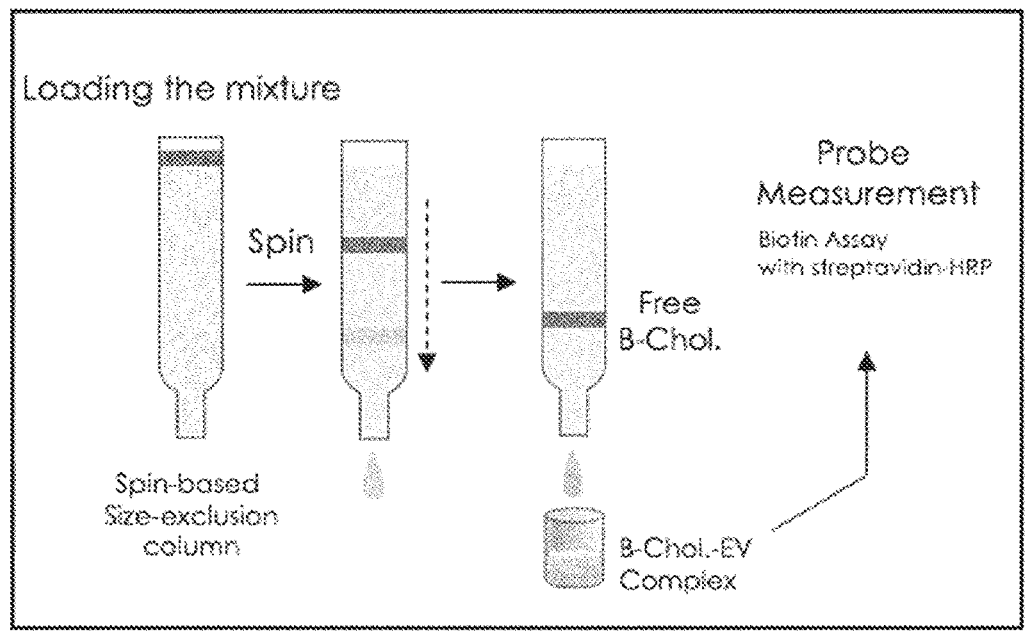

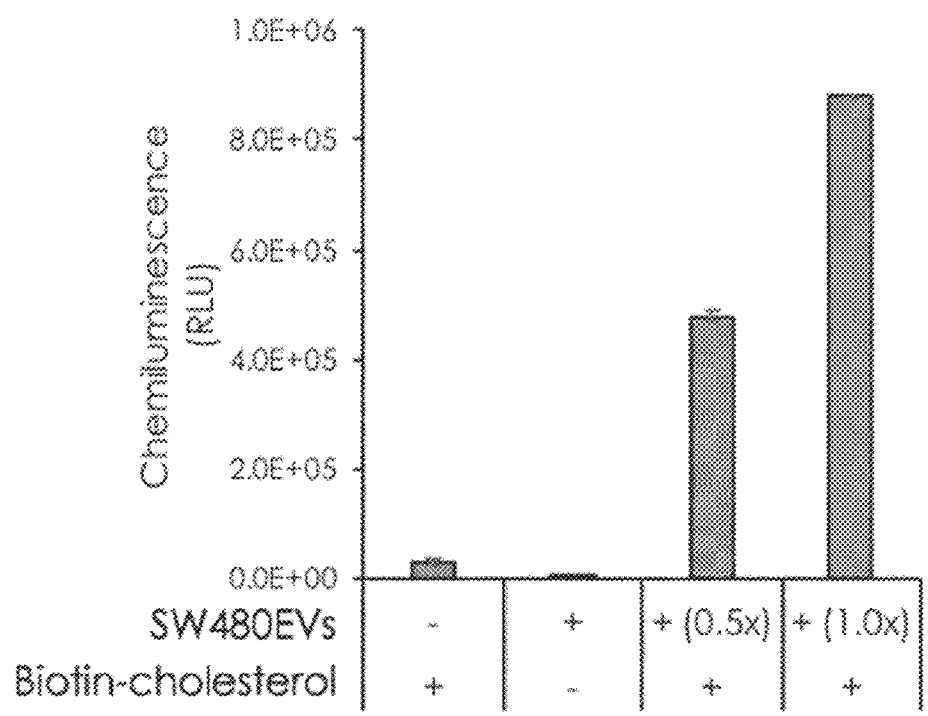

FIG. 17A
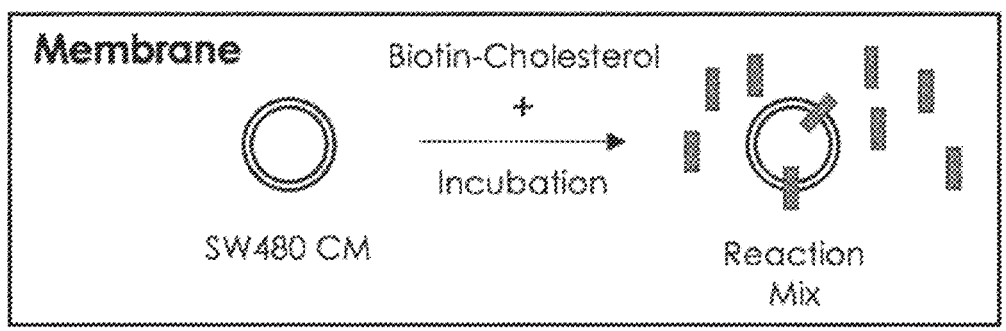
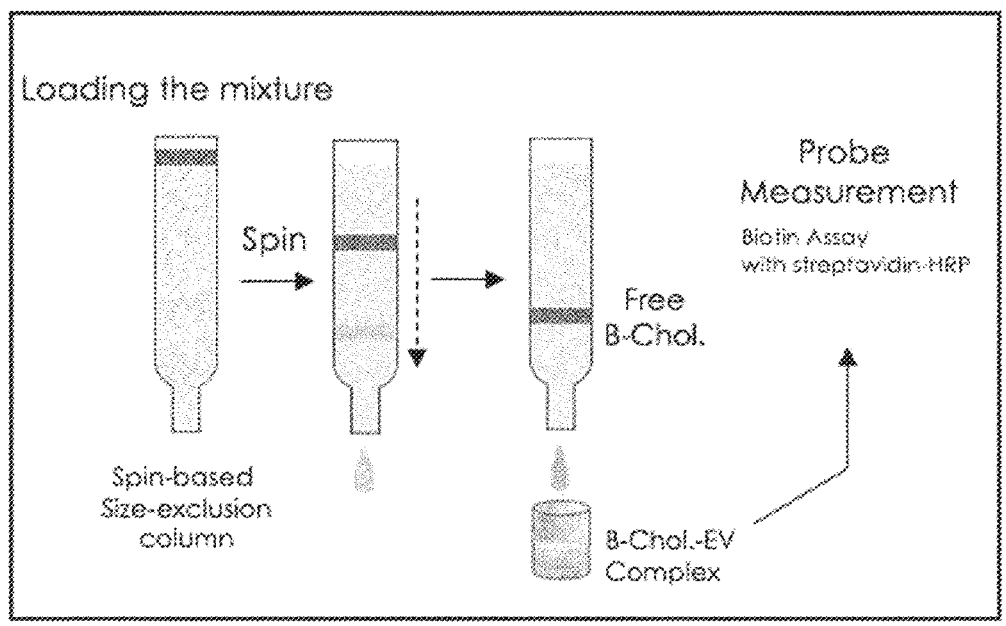

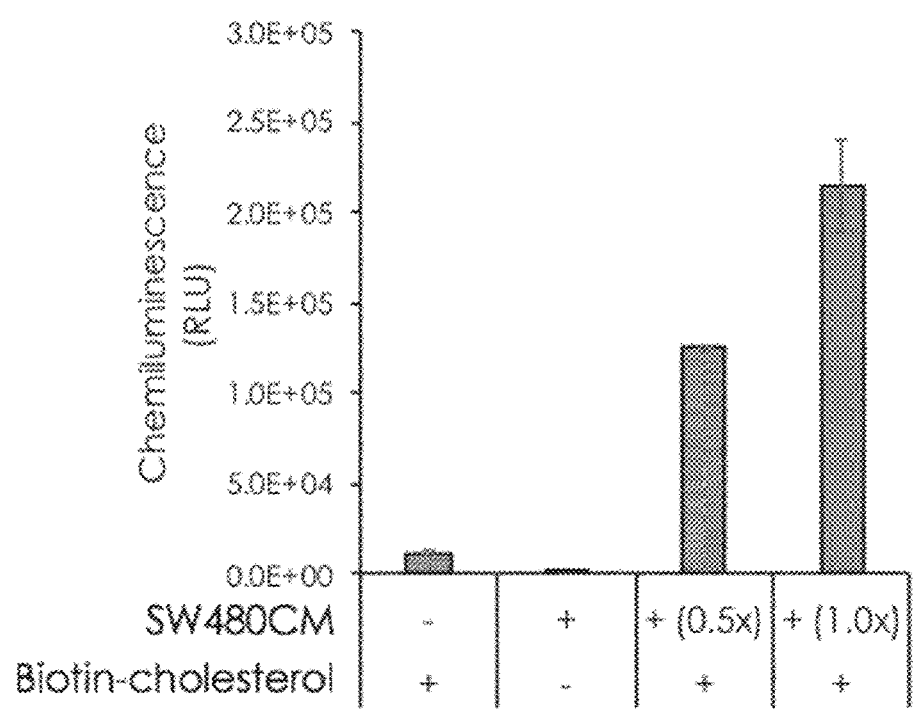

FIG. 20A
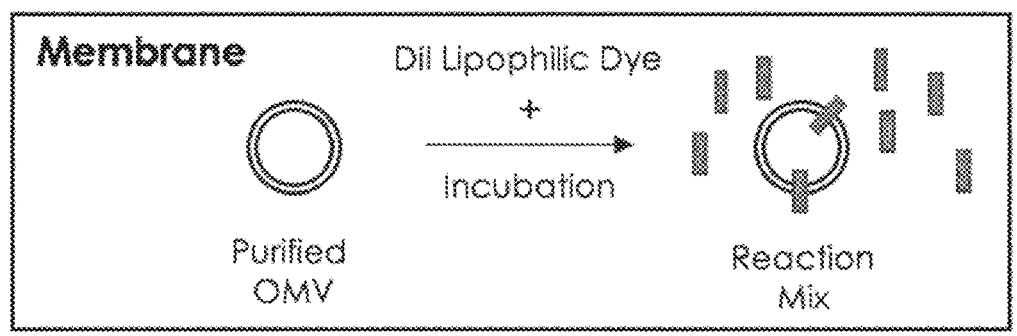
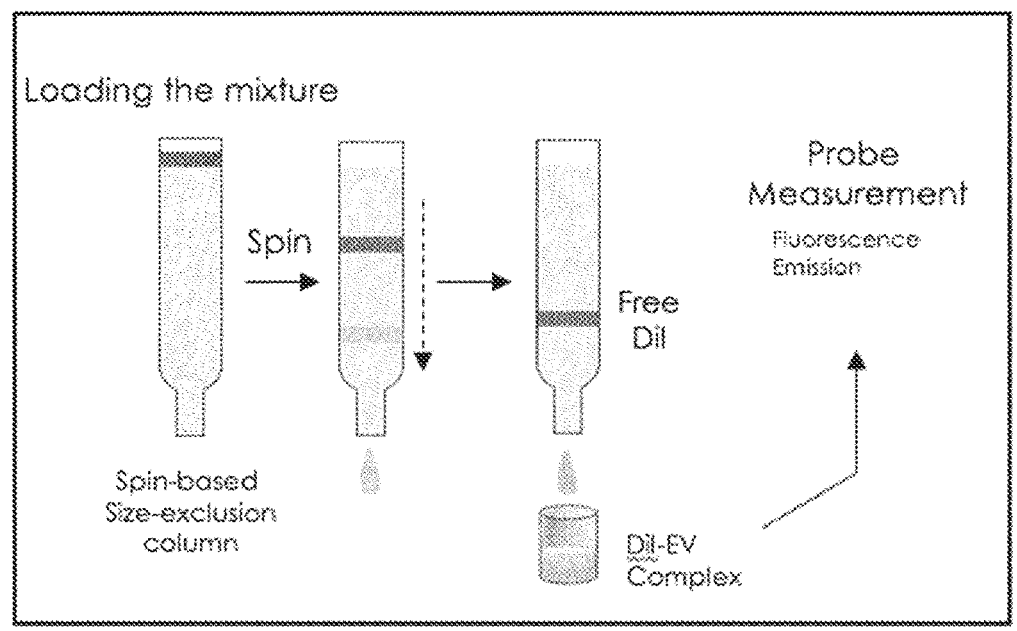

ANALYSIS METHOD FOR EXTRACELLULAR VESICLES, USING SIZE EXCLUSION CHROMATOGRAPHY, AND USE FOR SAME

TECHNICAL FIELD

The present invention relates to methods for analysis of extracellular vesicles using size-exclusion chromatography and uses thereof and, more specifically, to methods for analyzing extracellular vesicles contained in samples by using size-based fractionating ability of size-exclusion chromatography and probes specifically binding to extracellular vesicles.

BACKGROUND ART

Extracellular vesicles are nanoscale biological particles released from several types of cells in vivo or in vitro by a universal mechanism of cells, and are membrane vesicles that have various sizes in a range of 20-1,000 nm, are present in body fluids, such as blood, urine, saliva, and tears, and contain a lipid bilayer derived from cells.

These extracellular vesicles are involved in several important functions in various life phenomena. Extracellular vesicles derived from eukaryotic cells are involved in erythrocyte differentiation, immune response regulation, and the like, and especially, these extracellular vesicles have been revealed to play important roles in cancer progression, metastasis, or angiogenesis in cancer cell microenvironments and thus have received much attention in the application as a diagnostic marker for various diseases including cancer.

Extracellular vesicles released from prokaryotic cells contain components of prokaryotic cells similarly to extracellular vesicles from eukaryotic cells, cause not only systemic inflammations but also acute lung inflammation diseases depending on the entrance route thereof in the human body. These extracellular vesicles have been reported to induce chronic inflammatory responses in local skin tissues to thereby cause atopic dermatitis, one of the representative diseases of modern people. The extracellular vesicles derived from prokaryotic cells also have received much attention since bacteria-derived extracellular vesicles are reported to have correlation with various diseases including cancer in the human body.

Extracellular vesicles are composed of substances derived from mother cells, for examples, proteins, lipids, nucleic acids, and amino acids, and serve as carriers for carrying these substances in living bodies, so the analysis of proteins, lipids, nucleic acids, and amino acids constituting extracellular vesicles provides important bases for the understanding of physiological and pathological characteristics of mother cells. Therefore, the analysis of components of extracellular vesicles present in various samples has been receiving much attention in the basic and medical sciences.

In addition, it has been known that nucleic acids, growth hormones, proteins, and the like contained in the extracellular vesicles are protected by cellular membrane-type phospholipids and thus can perform more stable functions than soluble forms of growth factors and cytokines, and therefore, the extracellular vesicles are increasingly important, and the analysis of substances contained in the extracellular vesicles is expected to be utilized for various uses, including diagnosis and treatment of diseases.

In recent years, the utilization of non-invasive liquid biopsies in the diagnosis of diseases has been developed from various angles. Furthermore, efforts have been made to discover novel disease diagnostic markers by utilizing extracellular vesicles in body fluids and to develop diagnostic methods by using the markers. The key in the development of diagnostic methods is to promptly and accurately quantify target substances from small quantities of samples by using probes. It is therefore very important to analyze components of extracellular vesicles present in biological samples by using probes. However, this analysis of components of extracellular vesicles is conducted on the basis of the purification through ultracentrifugation with complicated steps and low efficiency. Such ultracentrifugation has a low yield in isolating extracellular vesicles and results in the inefficient removal of probes not binding to extracellular vesicles, and thus quantitative analysis using said method is nearly impossible in body fluids having relatively limited amounts and showing high complexity. There is therefore an urgent need to develop novel techniques that are distinguished from conventional analysis of extracellular vesicles and can perform prompt and simple procedures.

DETAILED DESCRIPTION OF THE INVENTION

Technical Problem

An aspect of the present invention is to provide a method for analysis of extracellular vesicles, the method comprising:
(a) mixing probes and a sample containing extracellular vesicles, followed by reaction, wherein each of the probes contains a binding portion specifically binding to components of the extracellular vesicles, and a detectable signal portion;
(b) injecting the mixed sample through a size-exclusion chromatography column, followed by development; and
(c) detecting extracellular vesicle-probe complexes and free probes from the developed sample.

Another aspect of the present invention is to provide a method for analysis of extracellular vesicles, the method comprising:
(a) mixing probes and a sample containing extracellular vesicles, followed by reaction, wherein each of the probes contains a binding portion specifically binding to components of the extracellular vesicles, and a detectable signal portion;
(b) injecting the mixed sample through a size-exclusion chromatography column, followed by development;
(c) separating extracellular vesicle-probe complexes from the size-exclusion chromatography column; and
(d) detecting the probes from the separated extracellular vesicle-probe complexes.

Technical Solution

The present invention has been made in view of the above-described problems, and an aspect of the present invention is to provide methods for analyzing extracellular vesicles by incubating samples with various substances, specifically binding to components of the extracellular vesicles, as probes to form extracellular vesicle-probe complexes, followed by development using size-exclusion chromatography, and then detecting the probes.

As used herein, the term "size-exclusion chromatography (SEC)" refers to a technique in which a mixture is separated on the basis of rates (permeability) at which various-sized solutes pass through a porous matrix. That is, the technique is based on a principle in which when a sample as a target of analysis is passed through a column packed with a porous stationary phase, such as a gel, a matrix, or beads, large molecules that cannot pass through pores of the column fail to enter the pores and quickly leave from the column through surrounding voids, while small molecules relatively slowly move through the pores of the column and leave the column. This method is generally used for desalting for buffer exchange, separation for purification, or molecular weight determination depending on solute size.

In the present invention, extracellular vesicle-probe complexes are formed by incubation of probes specifically binding to extracellular vesicles with various samples containing extracellular vesicles, and passed through a size-exclusion chromatography column, thereby fractionating the complexes and free probes promptly and easily, and then the thus separated eluates are analyzed in the next step, thereby easily and efficiently quantifying extracellular vesicles and analyzing components of extracellular vesicles.

As used herein, the term "extracellular vesicles" collectively refers to biological nanoparticles derived from cells of Archaea, Prokarya, or Eukarya, and examples thereof may include exosomes, argosomes, dexosomes, ectosomes, exovesicles, oncosomes, prominosomes, prostasomes, tolerosomes, microparticles, microvesicles, nanovesicles, blebbing vesicles, budding vesicles, exosome-like vesicles, matrix vesicles, membrane vesicles, shedding vesicles, membrane particles, shedding microvesicles, membrane blebs, epididimosomes, promininosomes, texosomes, or archeosomes, but are not limited thereto.

A method for analysis of extracellular vesicles according to the present invention is schematically shown in FIG. 1.

The method for analysis of extracellular vesicles according to the present invention comprises a step of mixing probes and a sample containing extracellular vesicles, followed by reaction, each of the probes containing: a binding portion specifically binding to components of the extracellular vesicles; and a detectable signal portion (step (a)).

As used herein, the term "probe" refers to a substance that specifically binds to a component constituting extracellular vesicles and is detectable and analyzable using spectroscopic analysis, physicochemical analysis, quantum chemical analysis, enzymatic analysis, or the like.

In the present invention, the probe may be (i) a single substance, which contains: a binding portion specifically binding to the component of extracellular vesicle; and a detectable signal portion, or (ii) a composite substance, in which a substance containing at least one analyzable signal portion is bound to a substance containing a binding portion specifically binding to the component of extracellular vesicle.

Extracellular vesicles are surrounded by a lipid bilayer and composed of substances derived from mother cells, for example, proteins, lipids, nucleic acids, and amino acids, which are distributed on the membrane surface of extracellular vesicles, in the surface of extracellular vesicles, or inside extracellular vesicles. In the present invention, the binding portion of the probe specifically binds to at least one component selected from the group consisting of membrane surface components of extracellular vesicles, membrane components of extracellular vesicles, and inside components of extracellular vesicles.

The probe may be selected from the group consisting of proteins, antibodies, antibody-derived substances, peptides, nucleic acids, nucleic acid-amino acid complexes, enzymes, enzyme substrates, chemical ligands, and compounds thereof, each of which specifically binds to at least one of the components constituting extracellular vesicles, but is not limited thereto. The probe may be a substance that not only specifically binds to a component of extracellular vesicles but is also detectable in a detection step. In an example of the present invention, VPD450 or CFDA-SE, which is one of the substrates for esterase as an inside component of extracellular vesicles, was used. Such a substrate not only specifically binds to esterase in extracellular vesicles, but can also be transformed into a fluorescent substance by enzymatic activity to thereby enable fluorescent signal detection without any separate label.

The probe of the present invention may further contain a detectable signal portion in addition to the substance specifically binding to at least one of the components constituting extracellular vesicles. The signal portion of the probe may be at least one selected from the group consisting of fluorescent substances, enzyme substrates, enzymes, proteins, peptides, nucleic acids, biotins, metals, and radioisotopes. According to an example of the present invention, a probe obtained by attaching a fluorescent label to an antibody recognizing a membrane surface protein of extracellular vesicles was used.

As used herein, the term "sample" encompasses biological samples or cell cultures containing extracellular vesicles, tissue samples, and the like, and specifically, the sample may be at least one selected from the group consisting of mammalian cell culture media, bacterial cell culture media, yeast culture media, tissue extracts, cancer tissues, serum, blood plasma, saliva, tears, aqueous humor, sweat, urine, feces, cerebrospinal fluid (CSF), ascites, amniotic fluids, semen, milk, dust, fresh water, seawater, soil, and fermented foods, but is not limited thereto.

The method for analysis of extracellular vesicles according to the present invention comprises a step of injecting the mixed sample through a size-exclusion chromatography column, followed by development (step (b)).

As used herein, the term "column" refers to a unit packed with a porous stationary phase used in size-exclusion chromatography, wherein the stationary phase means particles having various sizes of pores for fractionating substances by molecular weight. The resolution of separation by molecular size of molecules present in a sample depends on the size of the pores present in the stationary phase. For example, large pores present in the stationary phase are effective in the separation of relatively large molecules, and relatively smaller molecules are eluted without separation. Whereas, small pores present in the stationary phase result in a low degree of elution of large molecules, but may be effective in the separation of molecules having no smaller than a predetermined size and no larger than a predetermined size. Thus, a stationary phase having such a hole size to provide an optimum separation efficiency is generally selected considering the size of molecules to be separated and the size of contaminants in a sample. The most widely used gels in size-exclusion chromatography are series of Sepharose (GE Healthcare), Superose (GE Healthcare), Sephadex (Pharmacia), Bio-Gel P (Bio-Rad), and TSKgel® (Silica-based, Sigma). In an example of the present invention, Sephacryl S500, which has such a hole size to separate extracellular vesicles as nanoparticles from various sizes of proteins, was used, but is not limited thereto. The development of the size-exclusion chromatography of the present invention is carried out in a pump manner, a spin manner, or a gravity manner, but is not limited thereto.

The method for analysis of extracellular vesicles according to the present invention comprises a step of detecting extracellular vesicle-probe complexes and free probes from the developed sample (step (c)).

In the detecting step of the present invention, the extracellular vesicle-probe complex separated from the size-exclusion chromatography as well as the free probe not binding to the extracellular vesicles are detected to thereby obtain desired analysis results.

The detecting step of the present invention may comprise a step of quantifying extracellular vesicles by observing an absorption chromatogram at a predetermined wavelength. In the present invention, the predetermined wavelength may be at least one value selected from a range of 200-800 nm. In the present invention, the predetermined wavelength may be at least one wavelength in a range of 330-450 nm, or a wavelength of 230 nm, 260 nm, or 280 nm, but is not limited thereto.

The detecting step of the present invention may comprise a step of quantifying the probes by detecting the signal portion of the probes. Specifically, in the step of detecting the signal portion of the probes, appropriate detection and analysis methods according to the kind of signal portion of the probe may be selected, and may be selected from the group consisting of spectroscopic analysis (absorption, fluorescence, scattering, or radioactivity), physicochemical analysis, quantum chemical analysis, enzymatic analysis, biotin analysis, and nucleic acid analysis, but is not limited thereto.

The probe detecting step of the present invention includes direct analysis or indirect analysis depending on the property of the signal portion of the probes. In cases where the direct spectroscopic analysis is possible according to the light wavelength of the probes, analysis can be made by detecting a fluorescence signal, an absorption signal, a scattering signal, an emission signal, or a radioactive signal of the probe. In cases where the signal portion of the probe needs an additional treatment, an indirect analysis can be made by using biotin analysis, antibody analysis, enzyme analysis, polymerase chain reaction (PCR) analysis, or the like.

The present invention also provides a method for analyzing extracellular vesicles by separating extracellular vesicle-probe complexes from a sample and then analyzing the vesicle-probe complexes.

The method for analysis of extracellular vesicles according to the present invention comprises a step of mixing probes and a sample containing extracellular vesicles, followed by reaction, the probe containing: a binding portion specifically binding to components of the extracellular vesicles; and a detectable signal portion (step (a)) and a step of injecting the mixed sample through a size-exclusion chromatography column, followed by development (step (b)).

Detailed descriptions of the probe, sample, or size-exclusion chromatography of the present invention are as described above.

The method for analysis of extracellular vesicles according to the present invention comprises a step of separating extracellular vesicle-probe complexes from the size-exclusion chromatography column (step (c)).

In the extracellular vesicle-probe complex separating step of the present invention, the size-specific fractionation ability of size-exclusion chromatography is used. When the sample is passed through a size-exclusion chromatography column, the extracellular vesicles and other impurities contained in the sample are eluted in order of size and in order of time. In cases where a stationary phase having such a hole size to separate extracellular vesicles as nanoparticles from various sizes of proteins is used, the extracellular vesicles are relatively fast eluted since the extracellular vesicles have a molecular size of 1,000 kDa or more and thus are larger than free probes or other impurities. In the present invention, some of probes mixed with the sample specifically bind to form complexes and the other probes remain as free probes not binding to extracellular vesicles. The extracellular vesicle-probe complexes with relatively large sizes are fast eluted compared with the free probes. The elution time of each substance depends on the size of the porous stationary phase, the size of pores, the length of the column, the flow rate of a mobile phase, and the like, and the substance is eluted at a specific time in the same conditions.

The method for analysis of extracellular vesicles according to the present invention comprises a step of detecting the probes from the separated extracellular vesicle-probe complexes (step (d)).

A detailed description of the detecting step of the present invention is as described above.

In the detecting step of the present invention, quantitative analysis of extracellular vesicles and quantitative analysis of the probes binding to extracellular vesicles can be made, and the specificity or affinity for extracellular vesicles is analyzed according to the kind of probe, and can be utilized in evaluating probe performance.

Advantageous Effects

The methods for analysis of extracellular vesicles of the present invention use the size-specific fractionation ability of size-exclusion chromatography and the characteristics of probes specifically binding to extracellular vesicles, and the methods of the present invention can speed and facilitate a quantitative analysis of extracellular vesicles contained in samples, a physicochemical analysis of extracellular vesicles, an analysis of kinds and quantities of the components contained in extracellular vesicles, and an analysis of specificity or affinity of probes to the components of extracellular vesicles. In addition, the analysis method of the present invention can accurately analyze extracellular vesicles in samples without purification or pretreatment of the samples, and can simply and accurately analyze the components of extracellular vesicles according to the kinds of probes, and thus can improve the diagnosis efficiency using extracellular vesicles. Furthermore, the analysis method of the present invention can be utilized in extracellular vesicle-specific antibody screening, protein screening, chemical substance screening, and the like by using the analysis of specificity and affinity of probes.

BRIEF DESCRIPTION OF THE DRAWINGS

FIG. 2 shows a schematic diagram depicting the isolation of reference extracellular vesicles from colorectal cancer cell line SW480 and the isolation results according to an example of the present invention.

FIG. 5 shows UV (A) and fluorescence (B) chromatograms confirming the binding aspect of CD81 antibody (anti-CD81 antibody) labeled with a fluorescent substance and reference extracellular vesicles according to an example of the present invention.

FIG. 7 shows UV (A) and fluorescence (B) chromatograms confirming the expression profile of the CD81 extracellular vesicle marker in extracellular vesicles having different origins according to an example of the present invention.

FIG. 10 shows UV (A) and fluorescence (B) chromatograms confirming extracellular vesicles, without separate isolation of extracellular vesicles, from a colorectal cancer cell culture by using fluorescently labeled CD81 antibody according to an example of the present invention.

FIG. 12 shows UV (a) and fluorescence (B and C) chromatograms depicting the analysis of extracellular vesicles by using membrane-permeable violet proliferation dye 450 (VPD450) exhibiting fluorescence by esterase activity and esterase activity in reference extracellular vesicles according to an example of the present invention.

FIG. 13 shows UV (a) and fluorescence (b) chromatogram analysis results of extracellular vesicles in samples, without separation of extracellular vesicles, from colorectal cancer cell cultures by using esterase activity in extracellular vesicles and membrane-permeable violet proliferation dye 450 (VPD450) exhibiting fluorescence by esterase activity according to an example of the present invention.

FIG. 16 shows quantitative analysis results of biotin-cholesterol-extracellular vesicle complexes separated by spin-based size-exclusion chromatography of reference extracellular vesicles incubated with biotin-cholesterol according to an example of the present invention.

FIG. 17 shows quantitative analysis results of biotin-cholesterol-extracellular vesicle complexes separated by spin-based size-exclusion chromatography of colorectal cancer cell cultures incubated with biotin-cholesterol.

MODE FOR CARRYING OUT THE INVENTION

Hereinafter, the present invention will be described in more detail with reference to examples. These examples are intended to only illustrate the present invention, and it would be obvious to those skilled in the art that the scope of the present invention is not construed as being limited to the examples.

Example 1: Purification and Analysis of Reference Extracellular Vesicles

The colorectal cancer cell line SW480 culture medium was centrifuged at 500×g for 10 min and 2,000×g for 20 min to remove precipitates. To primarily purify and precipitate extracellular vesicles present in the supernatant, the supernatant was subjected to addition of a polyethylene glycol solution (8.4% polyethylene glycol 6000, 250 mM NaCl, 20 mM HEPES, pH 7.4), stored in a refrigerator for 16 h, and then centrifuged at 12,000×g for 30 min to harvest the precipitated extracellular vesicles, which were then dissolved in HEPES-buffered saline (20 mM HEPES, 150 mM NaCl, pH 7.4).

To secondarily purify extracellular vesicles by using density and buoyancy, the sample was subjected to 30%-20%-5% OptiPrep buoyant density gradient ultracentrifugation at 200,000×g for 2 h. After the ultracentrifugation, regions having an equivalent density (1.08-1.12 g/ml) to extracellular vesicles were harvested. To tertiarily purify the purified extracellular vesicles, the region was injected into a column (10×100 mm) packed with Sephacryl S500 using high performance liquid chromatography (HPLC) to obtain final extracellular vesicles through purification through molecular size-exclusion chromatography. The isolation scheme of reference extracellular vesicles is shown in FIG. 2A.

Ten region fractions were harvested from a surface of the sample obtained after the buoyant density gradient ultracentrifugation as a secondary purification method, and the distributions of extracellular vesicle markers (Alix, CD9, CD81, and CD63) in the respective fractions were investigated through western blotting. The results are shown in FIG. 2B. The reference extracellular vesicles finally isolated by the tertiary purification method were observed using a transmission electron microscope (TEM), and the results confirmed the shape and size (about 50-200 nm) of the purified reference extracellular vesicles (FIG. 2C).

Example 2: Analysis of Reference Extracellular Vesicles Using Pump-Type Size-Exclusion Chromatography and Fluorescently Labeled Antibodies To establish that the components of extracellular vesicles can be quantitatively analyzed by using the size-specific fractionation ability of size-exclusion chromatography and quantifying various kinds of probes recognizing the components of extracellular vesicles, the following tests were carried out.

2-1. Fluorescently Labeled Mouse Antibody (Normal Mouse IgG)

Figure 1:
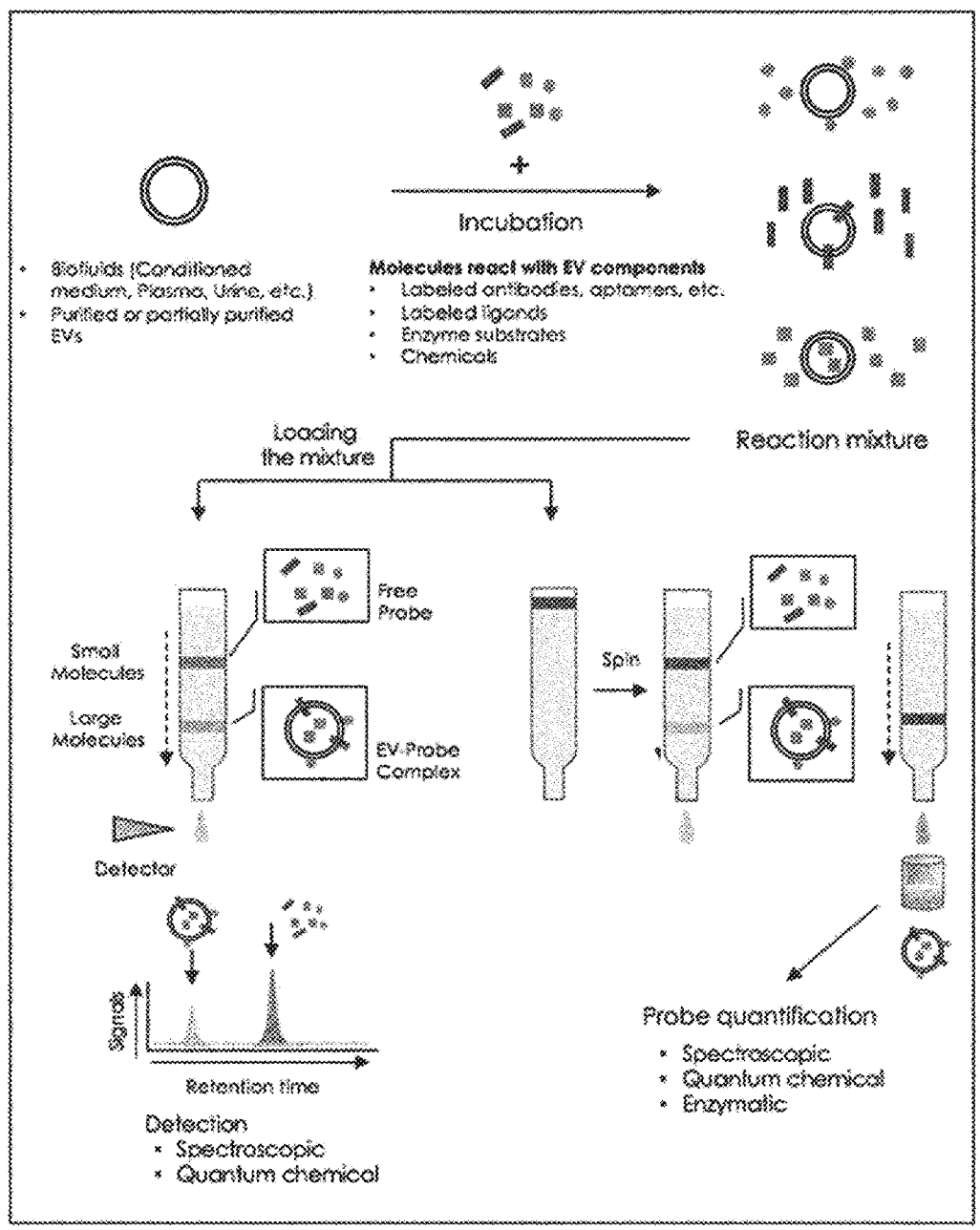
FIG. 1 is a schematic diagram of a method for analysis of extracellular vesicles according to an embodiment of the present invention.
Figure 3:
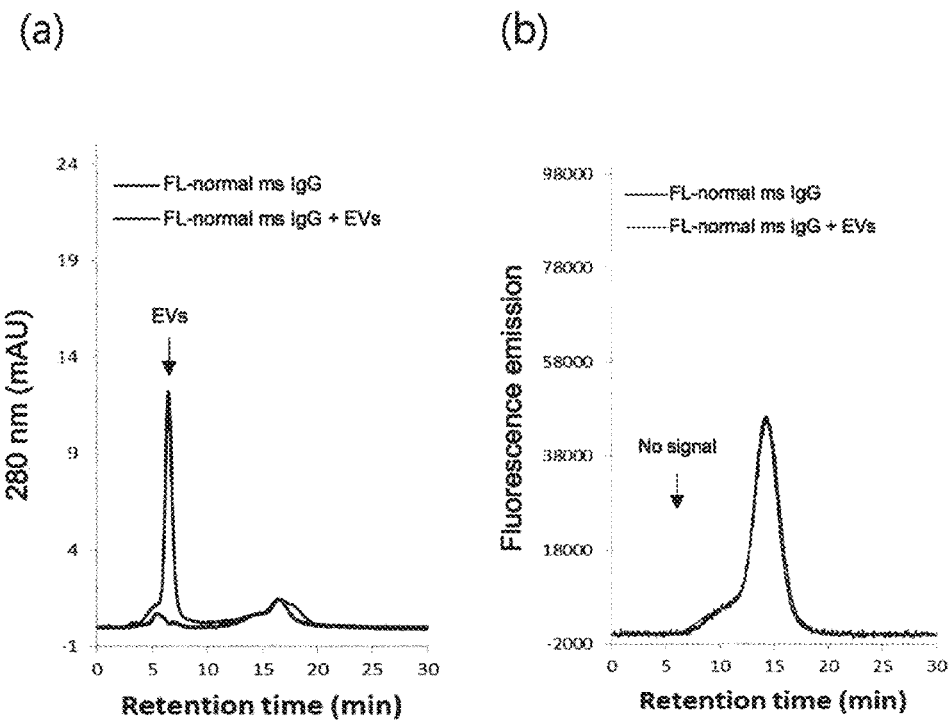
FIG. 3 shows UV (A) and fluorescence (B) chromatograms confirming the binding aspect of a mouse antibody (normal mouse IgG) labeled with a fluorescent substance and reference extracellular vesicles according to an example of the present invention.

The purified reference extracellular vesicles were mixed with a fluorescently labeled mouse antibody (normal mouse IgG), followed by incubation at 37° C. for 30 min, and then the mixture was injected into a column packed with Sephacryl S500 and developed using the HPLC system, and the 280 nm absorption chromatogram (FIG. 3A) and the fluorescence chromatogram (FIG. 3B) were analyzed.

The absorption chromatogram results confirmed that the reference extracellular vesicles were detected at 6.5 min and the antibody was detected at 14.5 min. In the fluorescence chromatogram, the fluorescence band of the fluorescently labeled antibody was detected at 14.5 min but no fluorescence band of the reference extracellular vesicles corresponding to the 6.5-min fraction was observed. The results showed that the reference extracellular vesicles and the mouse antibody did not have non-specific binding therebetween in the corresponding conditions and the mixture of the reference extracellular vesicles and the mouse antibody was effectively separated and eluted by size-exclusion chromatography.

2-2. Fluorescently Labeled Anti-CD63 and Anti-CD81 Antibodies (aCD63 and aCD81 Antibodies)

Figure 4:
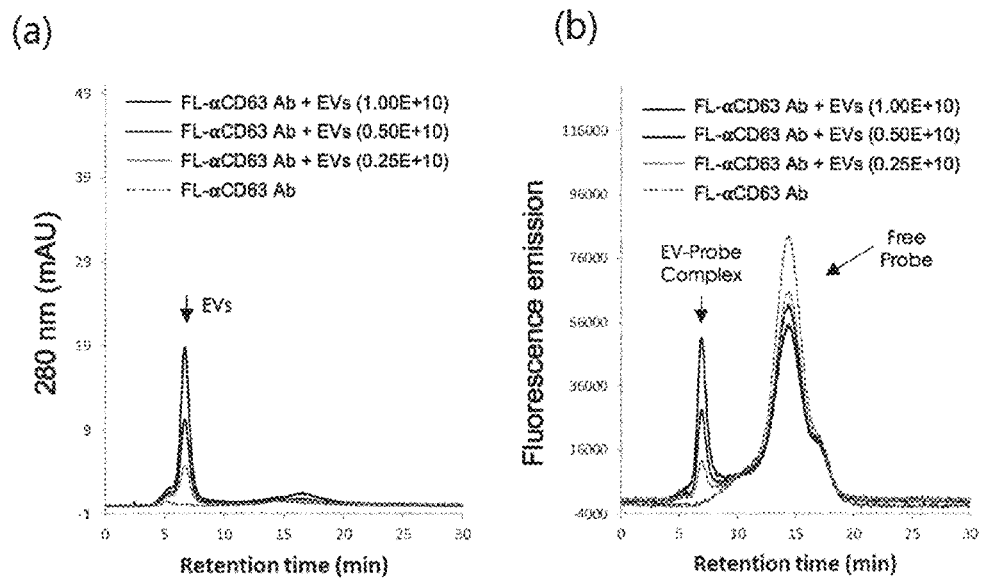
FIG. 4 shows UV (A) and fluorescence (B) chromatograms confirming the binding aspect of CD63 antibody (anti-CD63 antibody) labeled with a fluorescent substance and reference extracellular vesicles according to an example of the present invention.

Different amounts of the purified reference extracellular vesicles were mixed with fluorescently labeled anti-CD63 antibody (aCD63 antibody), which recognizes CD63, a membrane surface protein of extracellular vesicles, followed by incubation at 37° C. for 30 min, and then the mixture was injected into a column packed with Sephacryl S500 and developed using the HPLC system, and the 280 nm-absorption chromatogram (FIG. 4A) and the fluorescence chromatogram (FIG. 4B) were analyzed.

In addition, different amounts of the purified reference extracellular vesicles were mixed with fluorescently labeled anti-CD81 antibody (aCD81 antibody), which recognizes CD81, another membrane surface protein of extracellular vesicles, and then the mixture was developed by size-exclusion chromatography in the same conditions as above, and the 280 nm-absorption chromatogram (FIG. 5A) and the fluorescence chromatogram (FIG. 5B) were analyzed.

The results confirmed that, in the corresponding columns, the 280 nm-absorption bands of the reference extracellular vesicles were detected at 6.5 min and the fluorescence bands were observed at the same detection time, and the area of the detected band showed a high correlation with the amount of the reference extracellular vesicles injected. However, the fluorescence band area of the fluorescently labeled free antibody detected at 14.5 min decreased in inverse proportion to the amount of the reference extracellular vesicles injected. The results showed that the antibodies mixed with the reference extracellular vesicles specifically recognized the components (CD63 and CD81) of extracellular vesicles to bind with CD63 and CD81, respectively, thereby forming "extracellular vesicle-antibody complexes", and the relatively small-molecular weight fluorescently labeled antibodies (detected at 14.5 min) were developed together with extracellular vesicles corresponding to macro molecules, resulting in the detection of fluorescence bands at the detection time of extracellular vesicles (6.5 min). Furthermore, the results showed that the area of the fluorescence band detected at the detection time of the fluorescently labeled free antibody reflected the amount of free antibodies, which corresponded to the total amount of antibodies mixed with the sample minus the amount of antibodies binding to the extracellular vesicles.

2-3. Competitive Binding of Anti-CD63 Antibody

To investigate whether a fluorescence label had an effect on the specific binding when the fluorescently labeled anti-CD63 antibody specifically recognized CD63 present in the reference extracellular vesicles to form a complex, the extracellular vesicles were mixed with fluorescently labeled anti-CD63 antibody and unlabeled anti-CD63 antibody, followed by incubation. Specifically, a comparison of fluorescence chromatogram through size-exclusion chromatography was made between a group of the reference extracellular vesicles mixed with fluorescently labeled anti-CD63 antibody and a group of the reference extracellular vesicles mixed with a ratio of 1:10 of fluorescently labeled anti-CD63 antibody and fluorescently unlabeled anti-CD63 antibody.

Figure 6:
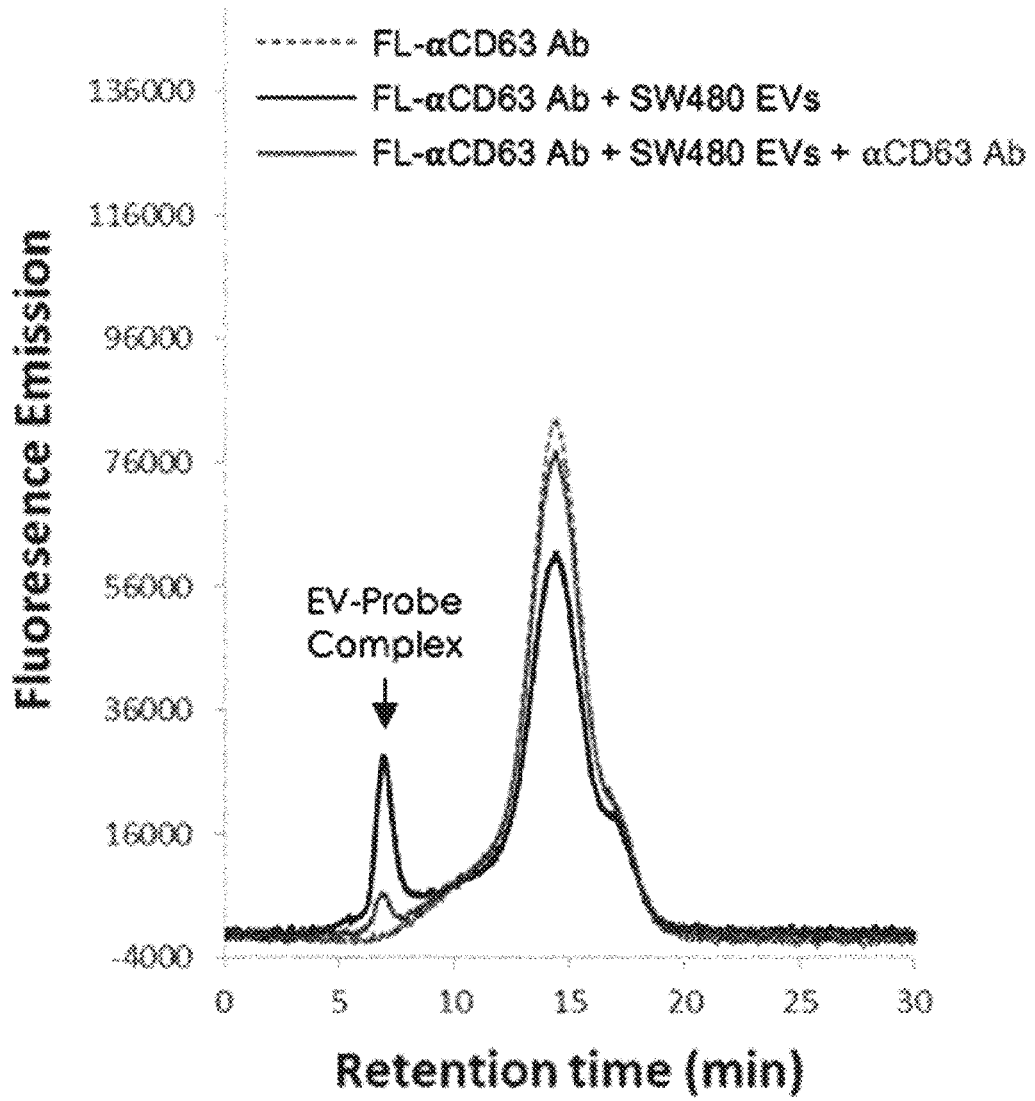
FIG. 6 shows a fluorescence chromatogram confirming specificity of fluorescently labeled CD63 antibody in reference extracellular vesicles according to an example of the present invention.

The results confirmed that the fluorescence band of the extracellular vesicle-antibody complex significantly decreased in the group in which the excessive fluorescently unlabeled anti-CD63 antibody was further added (FIG. 6). These results showed that the excessive fluorescently unlabeled anti-CD63 antibody binds to CD63 of the extracellular vesicles to inhibit the binding of the fluorescently labeled anti-CD63 antibody, resulting in a significant decrease in amount of the fluorescently labeled anti-CD63 antibody binding to the extracellular vesicles, indicating that the binding between extracellular vesicles and anti-CD63 antibody is very specific and a fluorescent label does not have an effect on the functions of the anti-CD63 antibody.

2-4. Extracellular Vesicles Released from Different Kinds of Mother Cells and Fluorescently Labeled Anti-CD81 Antibody By mixing equivalent amounts of extracellular vesicles releases from different kinds of mother cells (SW480 and HMEC1) with an equivalent amount of fluorescently labeled anti-CD81 antibody, the expression profiles of CD81 protein in the respective kinds of extracellular vesicles were analyzed through the 280 nm-absorption chromatogram (FIG. 7A) and the fluorescence chromatogram (FIG. 7B) using the size-exclusion chromatography.

The results showed that in the corresponding columns, the areas of the 280 nm-absorption bands detected at 6.5 min were the same for the respective kinds of extracellular vesicles, but the areas of the fluorescence bands of the complexes of the respective kinds of extracellular vesicles and anti-CD81 antibody detected at the same detection time (6.5 min) were different. The fluorescence was significantly lower in the HMEC1 cell-derived extracellular vesicles than the SW480 colorectal cancer cell-derived extracellular vesicles, and the area of the fluorescence band of the free antibody at 8.5 min was higher in the HMEC1 cell-derived extracellular vesicles. The reason is that the amount of extracellular vesicles per unit sample depends on the kind of mother cells, indicating that the relative amounts of respective components per unit of extracellular vesicles can be promptly determined by the analysis method of the present invention in the analysis of several kinds of extracellular vesicles.

2-5. Component Change of Extracellular Vesicles According to Treatment with or without TNFα

Figure 8:
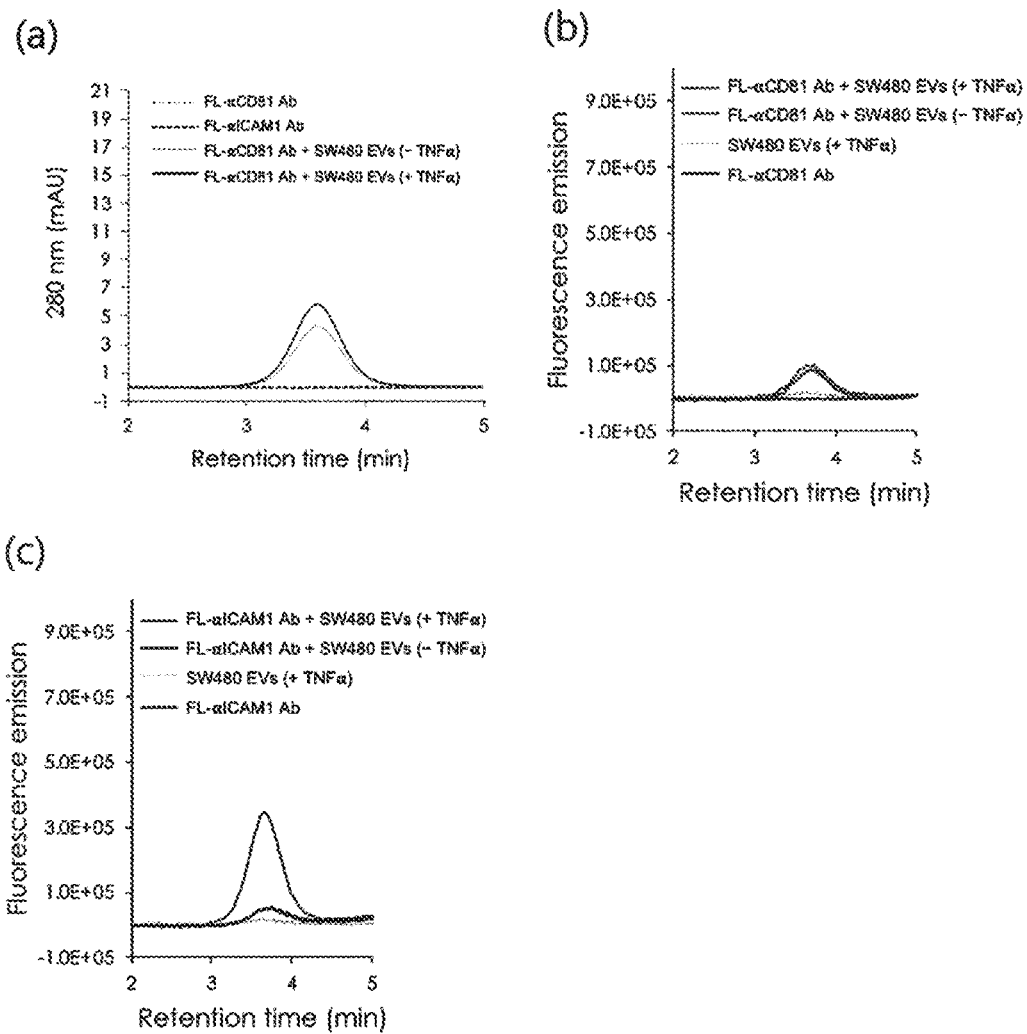
FIG. 8 shows UV (A) and fluorescence (B and C) chromatograms analyzing the effect of tumor necrosis factor alpha (TNFα) on the expression of ICAM1 protein of extracellular vesicles released from colorectal cancer cells.

The method of the present invention was used to analyze the effect of TNFα on the component change of extracellular vesicles released from colorectal cancer cells. Specifically, colorectal cancer cells, when cultured, were divided into a group with TNFα treatment for 24 h (TNFα+) and a group without TNFα treatment (TNFα−), and the extracellular vesicles in the respective cell culture media were purified by a conventional method. The extracellular vesicles purified in the respective groups were mixed with fluorescently (FITC) labeled anti-CD81 antibody and fluorescently (PE) labeled anti-ICAM1 antibody, followed by incubation, and the mixtures were injected and developed in the size-exclusion chromatography columns, and the 280 nm-absorption chromatogram (FIG. 8A) and the fluorescence chromatograms (FIGS. 8B and 8C) were analyzed.

The results confirmed that in the corresponding columns, the areas of the 280 nm-absorption bands (A) and the areas of fluorescence bands (B) of CD81 of the extracellular vesicles detected at 3.6 min for the respective cases were similar, but the fluorescence band (C) of ICAM1 detected at the same detection time (3.6 min) significantly increased in the TNFα+ group than the TNFα− group. The results showed that after TNFα treatment, the amount of CD81 protein in the extracellular vesicles was little changed but the amount of ICAM1 protein significantly increased. The results indicated that the physiological changes of cells, caused by cell conditions, environments, or external factors, lead to the component change of extracellular vesicles released from cells, even from homogeneous cells, and such changes can be easily analyzed by the method of the present invention.

Briefly, the present analysis method can be simply and promptly utilized in the analyses of the total amount of extracellular vesicles and the components of extracellular vesicles in samples as well as the analyses of specificity and affinity of antibodies and ligands to the components of extracellular vesicles.

Example 3: Analysis of Extracellular Vesicles in Cell Cultures Using Pump-Type Size-Exclusion Chromatography and Fluorescently Labeled Antibodies 3-1. Fluorescently Labeled Anti-C63 Antibody To analyze the amount or components of extracellular vesicles in the cell culture using the analysis method of the present invention, SW480 colorectal cancer cells were cultured in RPMI media for 24 h to harvest the cell culture. A group of RPMI medium without cell culture mixed with fluorescently labeled anti-CD63 antibody and a group of a colorectal cancer cell culture mixed with fluorescently labeled anti-CD63 antibody were incubated at 37° C. for 30 min, and injected into TSK6000 HPLC column, followed by development using the HPLC system, and a fluorescence chromatogram was analyzed.

Figure 9:
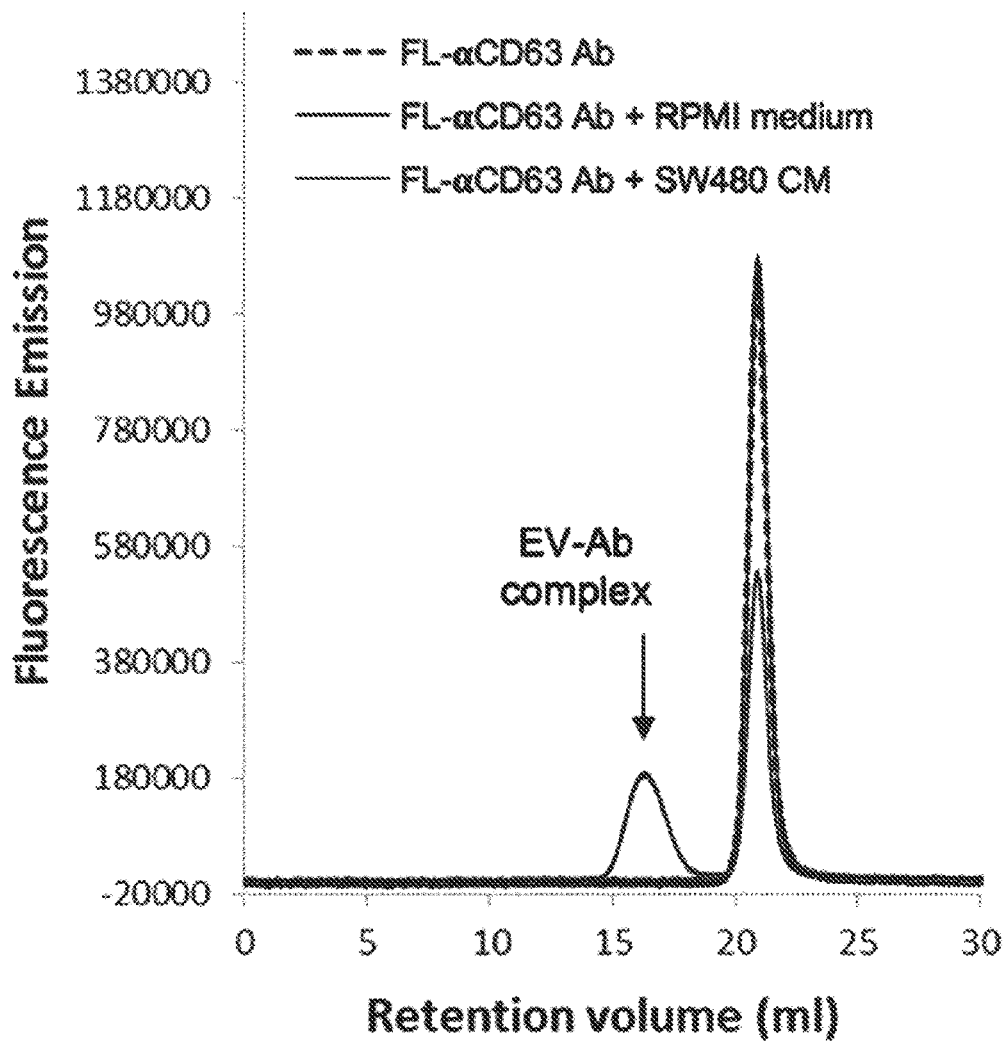
FIG. 9 shows a fluorescence chromatogram confirming extracellular vesicles, without separate isolation of extracellular vesicles, from a colorectal cancer cell culture by using fluorescently labeled CD63 antibody according to an example of the present invention.

As a result, as shown in FIG. 9, only the fluorescence band of the free antibody detected at 22 min was observed in the group of RPMI medium mixed with fluorescently labeled anti-CD63 antibody, but additional fluorescence band was detected at 17 min together with the fluorescence band of the free antibody at 22 min in the group of a colorectal cancer cell culture mixed with fluorescently labeled anti-CD63 antibody. In addition, the area of the fluorescence band detected at 22 min in the sample containing a colorectal cancer cell culture was about 50% the area of the fluorescence band in the group of RPIM media mixed with fluorescently labeled anti-CD63 antibody. These results showed that about 50% of the fluorescently labeled anti-CD63 antibody specifically bound to CD63 protein of extracellular vesicles in the cell culture to form an "extracellular vesicle-antibody complex", and thus such the fluorescently labeled anti-CD63 antibody was developed together with the extracellular vesicles, resulting in a 17 min-fluorescence band. It can be therefore seen that by using the analysis method, a component of extracellular vesicles in a cell culture can be analyzed even without separate purification of extracellular vesicles from the cell culture.

3-2. Fluorescently Labeled Anti-C81 Antibody

Similar to 3-1 above, the colorectal cancer cell culture was mixed with fluorescently labeled anti-CD81 antibody, followed by incubation at 37° C. for 30 min, and the mixture was injected into the Sephacryl S500 column and developed using the HPLC system, and the 280 nm-absorption chromatogram (FIG. 10A) and the fluorescence chromatogram (FIG. 10B) were analyzed.

As a result, both the 280 nm-absorption band and the fluorescence band were detected at 3.5 min in the corresponding columns. These results confirmed that the extracellular vesicles expressed CD81 protein, indicating that a component of extracellular vesicles in samples can be analyzed without separate purification of extracellular vesicles.

3-3. Analysis of Extracellular Vesicles Over Time of Culture

Figure 11:
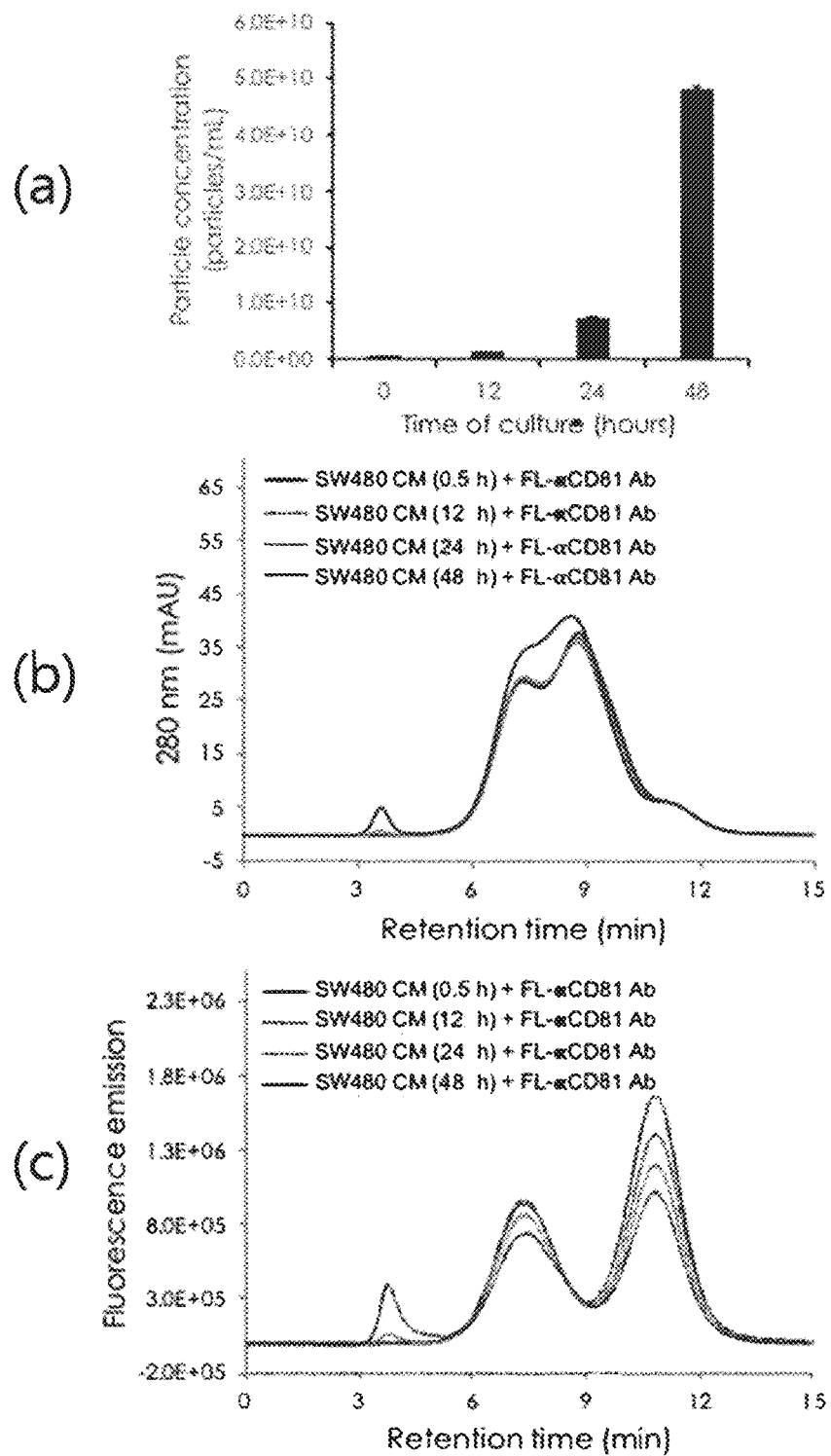
FIG. 11 shows the analysis results of nanoparticle concentration (A), UV (B), and fluorescence (C) chromatograms confirming extracellular vesicles in samples, without separate isolation of extracellular vesicles, from colorectal cancer cell cultures at different times of culture by using fluorescently labeled CD81 antibody according to an example of the present invention.

To investigate the aspect of extracellular vesicles released during cell growth, respective colorectal cancer cell cultures with different times of culture were mixed with an equivalent amount of fluorescently labeled anti-CD81 antibody, followed by incubation at 37° C. for 30 min, and then the mixtures were injected into Sephacryl S500 columns and developed using the HPLC system. The nanoparticle concentration (FIG. 11A), the 280 nm-absorption chromatogram through the size-exclusion chromatography (FIG. 11B), and the fluorescence chromatogram (FIG. 11C) were analyzed for the respective cell cultures.

The results showed through the nanoparticle concentration analysis that as the time of culture of colorectal cancer cells increased, the nanoparticle concentration in the cell culture increased. The size-exclusion chromatography results confirmed that as the time of culture of colorectal cancer cells increased, both the 280 nm-absorption band and the fluorescence band of CD81 antibody increased at 3.6 min at which the extracellular vesicles were eluted, indicating that the time of culture has a high correlation with an increase in nanoparticle concentration in a cell culture. The results indicated that the method of the present invention can be used to analyze both the relative amount and components of extracellular vesicles in a sample without separate purification of extracellular vesicles.

Example 4: Analysis of Reference Extracellular Vesicles Using Pump-Type Size-Exclusion Chromatography and Membrane-Permeable Enzyme Substrate In the method of the present invention, to investigate the possibility of quantitative analysis of the components of extracellular vesicles by using a probe or enzyme recognizing an inner component of extracellular vesicles, VPD450 was used, wherein VPD450 is a substrate of esterase as one of enzymes present inside extracellular vesicles, has membrane permeable properties, and is transformed into a fluorescent substance by enzymatic activity. Specifically, the purified reference extracellular vesicles, fluorescently labeled anti-CD81 antibody, and different concentrations of VDP450 were mixed, incubated at 37° C. for 30 min, injected into the Sephacryl S500 column, and developed using the HPLC system, and the 280 nm-absorption chromatogram (FIG. 12A) and the fluorescence chromatograms (FIGS. 12B and 12C) were analyzed.

The results confirmed through the 280 nm-absorption bands that the reference extracellular vesicles were detected at 3.5 min in the corresponding columns, and confirmed through the fluorescence chromatogram results that both the fluorescence band of anti-CD81 antibody and the fluorescence band of VPD450 were observed at the same elution time. It can be therefore seen that the reference extracellular vesicles expressed both CD81 protein and esterase. It can also be seen that the area of the fluorescence band of VPD450 was proportional to the concentration of VPD450, and as the VPD450 concentration increased, the fluorescent enzymatic active product was accumulated in extracellular vesicles. Meanwhile, it can be seen that the fluorescent product of VPD450 generated by natural hydrolysis (the peak coming later in FIG. 12C) has a small molecular size and thus were clearly distinguished through size-exclusion chromatography.

Example 5: Analysis of Extracellular Vesicles in Cell Culture Using Pump-Type Size-Exclusion Chromatography and Membrane-Permeable Enzyme Substrate To prove that the analysis of extracellular vesicles using a substrate for an enzyme present inside extracellular vesicles, verified in Example 4, was possible in biological samples even without additional purification of extracellular vesicles, a test was carried out using cell cultures. Specifically, the SW480 colorectal cancer cell culture and the membrane-permeable VDP450 were mixed, incubated at 37° C. for different times, injected into the Sephacryl S500 columns, and developed using the HPLC system, and the 280 nm-absorption chromatogram (FIG. 13A) and the fluorescence chromatogram (FIG. 13B) were analyzed.

As a result, in the corresponding columns, the area of the 280 nm-absorption band of reference extracellular vesicles detected at 3.5 min was constant regardless of the time of incubation, but the fluorescence band increased depending on the time of incubation. The reason is that the esterase inside extracellular vesicles transformed VPD450, flowing into extracellular vesicles, into a fluorescent substance in proportion to the time of incubation, and the transformed fluorescent substance was accumulated inside the extracellular vesicles. It can be seen that the above method can be utilized in the analysis of the total amount of extracellular vesicles in biological samples even without purification of extracellular vesicles when the amount of substrates or the time of incubation was fixed.

Figure 14A:
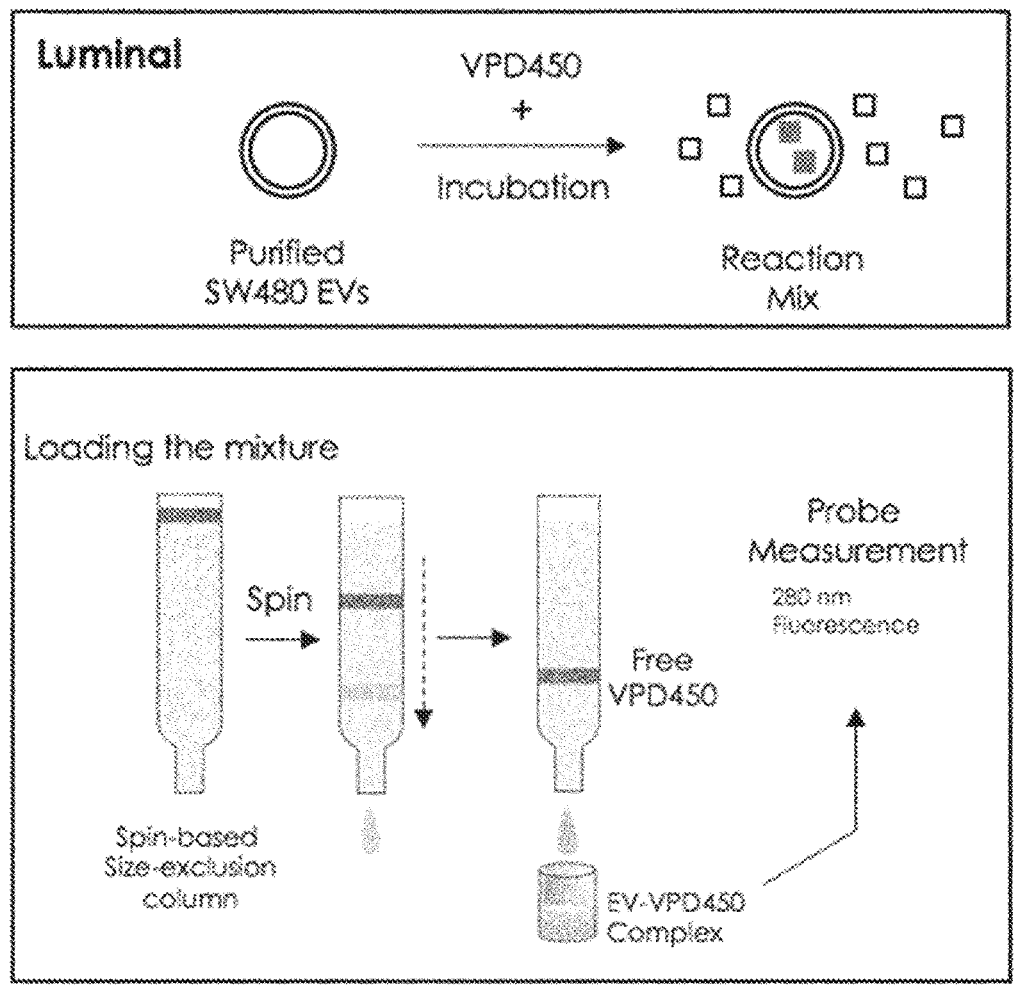
FIG. 14 shows UV and fluorescence chromatogram analysis results (B) of fluorescence substance-bound reference extracellular vesicles by using membrane-permeable violet proliferation dye 450 (VPD450) exhibiting fluorescence by esterase activity and spin-based size-exclusion chromatography according to an example of the present invention.

Example 6: Analysis of Reference Extracellular Vesicles Using Spin-Based Size-Exclusion Chromatography and Membrane-Permeable Enzyme Substrate 6-1. Reference Extracellular Vesicle-Fluorescent VPD450 Complex In the method for analysis of extracellular vesicles using the membrane-permeable enzyme substrate, as shown in the schematic diagram of FIG. 14A, the extracellular vesicle-fluorescent VPD450 complex was separated from a substance not reacting with extracellular vesicles, and then the separated complex was analyzed. Specifically, the reference extracellular vesicles were mixed with the membrane-permeable substrate VPD450, followed by incubation, and then the mixture was loaded in the spin-based Sephacryl S500 column, followed by centrifugation, to thereby harvest an eluate. The eluted extracellular vesicle-fluorescent VPD450 complex was injected into the Sephacryl S500 column and developed using the HPLC system, and the 280 nm-absorption and fluorescence chromatograms (FIG. 14B) were analyzed.

As a result, as for the reference extracellular vesicles not reacting with VPD450, only the 280 nm-absorption band was detected at 3.5 min and the fluorescence band was not detected at the same time, but as for the samples pretreated using the spin-based size-exclusion chromatography, the 280 nm-absorption band and the strong VPD450 fluorescence band were detected at 3.5 min. The results indicated that small molecular substances not reacting extracellular vesicles are effectively removed through pretreatment.

6-2. Reference Extracellular Vesicle-CFDA-SE Complex

Figure 15B:
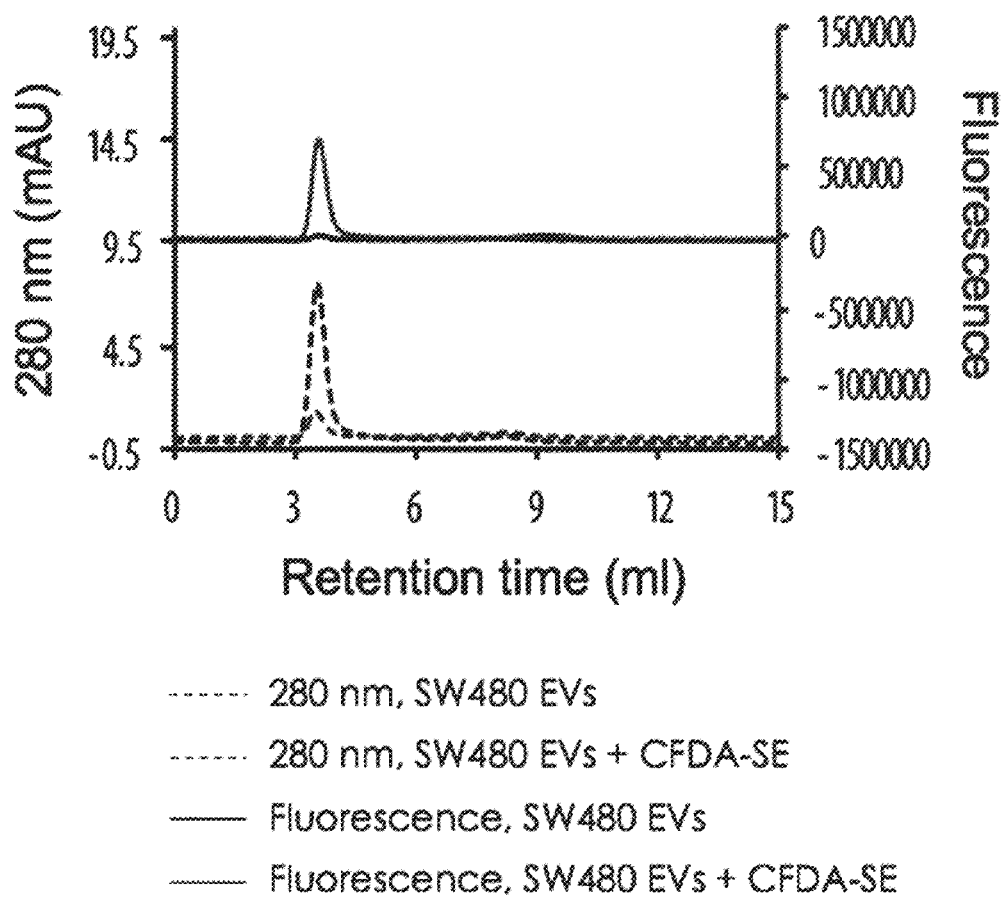
FIG. 15 shows UV and fluorescence chromatogram analysis results (B) of fluorescence substance-bound reference extracellular vesicles by using membrane-permeable carboxyfluorescein diacetate succinimidyl ester (CFDA-SE) exhibiting fluorescence by esterase activity and spin-based size-exclusion chromatography according to an example of the present invention.

As shown in the schematic diagram of FIG. 15A, the reference extracellular vesicles were mixed with CFDA-SE, another esterase substrate, followed by incubation, to thereby obtain solutions, and then the solutions were pretreated by the method shown in 6-1 above, injected into the Sephacryl S500 column, and developed using the HPLC system, and the 280 nm-absorption and fluorescence chromatograms (FIG. 15B) were analyzed.

As a result, in the corresponding columns, the 280 nm-absorption band was detected at 3.5 nm and the fluorescence band was detected at the same time, indicating that CFDA-SE also permeates through the membrane according to the same mechanism as in VPD450, becomes a fluorescent substance by activity of esterase inside the extracellular vesicles, and the fluorescent substance is accumulated inside extracellular vesicles.

Therefore, by using a method comprising the step of separating extracellular vesicles, the total amount of extracellular vesicles in samples can be analyzed, and such a method can be utilized in various tracking studies using extracellular vesicles through the provision of purified probe-extracellular vesicle complexes.

Example 7: Analysis of Extracellular Vesicles Using Spin-Based Size-Exclusion Chromatography and Cholesterol Probe (Biotinylated Cholesterol)

To establish that the total amount of extracellular vesicles can be determined by quantifying a probe, which binds to or is inserted into (transmembrane) a lipid bilayer of the components of extracellular vesicles, by using size-exclusion chromatography analysis, biotin-cholesterol was used as a probe.

Specifically, as shown in the schematic diagram of FIG. 16A, different amounts of the purified reference extracellular vesicles were mixed with biotin-cholesterol, followed by incubation at 37° C. for 30 min, and then, for the removal of biotin-cholesterol not binding to extracellular vesicles, the respective mixture solutions were loaded in the spin-based Sephacryl S500 columns, followed by centrifugation at 700×g for 5 min, to thereby harvest eluates. A biotin-cholesterol single group or a reference extracellular vesicle single group as a control was loaded in the column by the same method as above, followed by spinning, to thereby harvest an eluate. To quantify biotin in the eluates, the eluates were placed in 96-well plates (microplates), and then substances in samples were adsorbed and fixed to the plate. Thereafter, the plates were incubated with streptavidin-peroxidase, followed by washing, and then the chemiluminescence was measured according to the activity of peroxidase remaining on the plates (FIG. 16B).

As a result, the chemiluminescence was little observed in the biotin-cholesterol single group or the reference extracellular vesicle single group. The results showed that the small molecular weight biotin-cholesterol was not eluted from the spin-based size-exclusion chromatograms, indicating that the large-molecular weight extracellular vesicles were eluted from the spin-based size-exclusion chromatography column, like in the results of FIG. 15, but biotin capable of binding with streptavidin-peroxidase was not present in the eluted reference extracellular vesicles per se. On the other hand, a high chemiluminescence was observed in the groups in which the reference extracellular vesicles and biotin-cholesterol were mixed and incubated, and the intensity of chemiluminescence increased in proportion to the amount of reference extracellular vesicles. These results indicated that the relatively small-molecular weight biotin-cholesterol is inserted into a lipid bilayer constituting extracellular vesicles and can be eluted together with the large-molecular weight extracellular vesicles from the spin-based size-exclusion chromatography column, and the degree of insertion of biotin-cholesterol into the lipid bilayer is proportional to the amount of extracellular vesicles.

Example 8: Analysis of Extracellular Vesicles in Colorectal Cancer Cell Cultures Using Spin-Based Size-Exclusion Chromatography and Cholesterol Probe It was proved in Example 7 that from the mixture of reference extracellular vesicles and biotin-cholesterol, only the biotin-cholesterol-extracellular vesicle complex could be effectively separated through the spin-based size-exclusion chromatography pretreatment. To investigate whether the total amount of extracellular vesicles in a cell culture could be analyzed without purification of extracellular vesicles by the above method, the SW480 colorectal cancer cell culture and biotin-cholesterol were used. Specifically, as shown in the schematic diagram of FIG. 17A, different concentrations of SW480 colorectal cancer cell cultures were mixed with biotin-cholesterol, followed by incubation at 37° C. for 30 min. Then, for the removal of biotin-cholesterol not binding to extracellular vesicles in the samples, the respective mixture solutions were loaded in spin-based Sephacryl S500 columns, followed by centrifugation at 700×g for 5 min, to thereby harvest eluates. A biotin-cholesterol single group or a colorectal cancer cell culture single group as a control was loaded in the column by the same method as above, followed by spinning, to thereby harvest an eluate. To quantify biotin in the eluates, the eluates were placed in 96-well plates (microplates), and then substances in the samples were adsorbed and fixed to the plates. Thereafter, the plates were incubated with streptavidin-peroxidase and washed, and then the chemiluminescence was measured according to the activity of peroxidase remaining on the plates (FIG. 17B).

As a result, the chemiluminescence was observed to be very low or absent in the biotin-cholesterol single group and the colorectal cancer cell culture single group, but a high chemiluminescence was observed in the groups in which the colorectal cancer cell culture and biotin-cholesterol were mixed and incubated. These results proved that the biotin-cholesterol molecules are inserted into the lipid bilayer of extracellular vesicles in a cell culture and can be eluted together with extracellular vesicles from the spin-based pretreatment size-exclusion chromatography column.

Figure 18A:
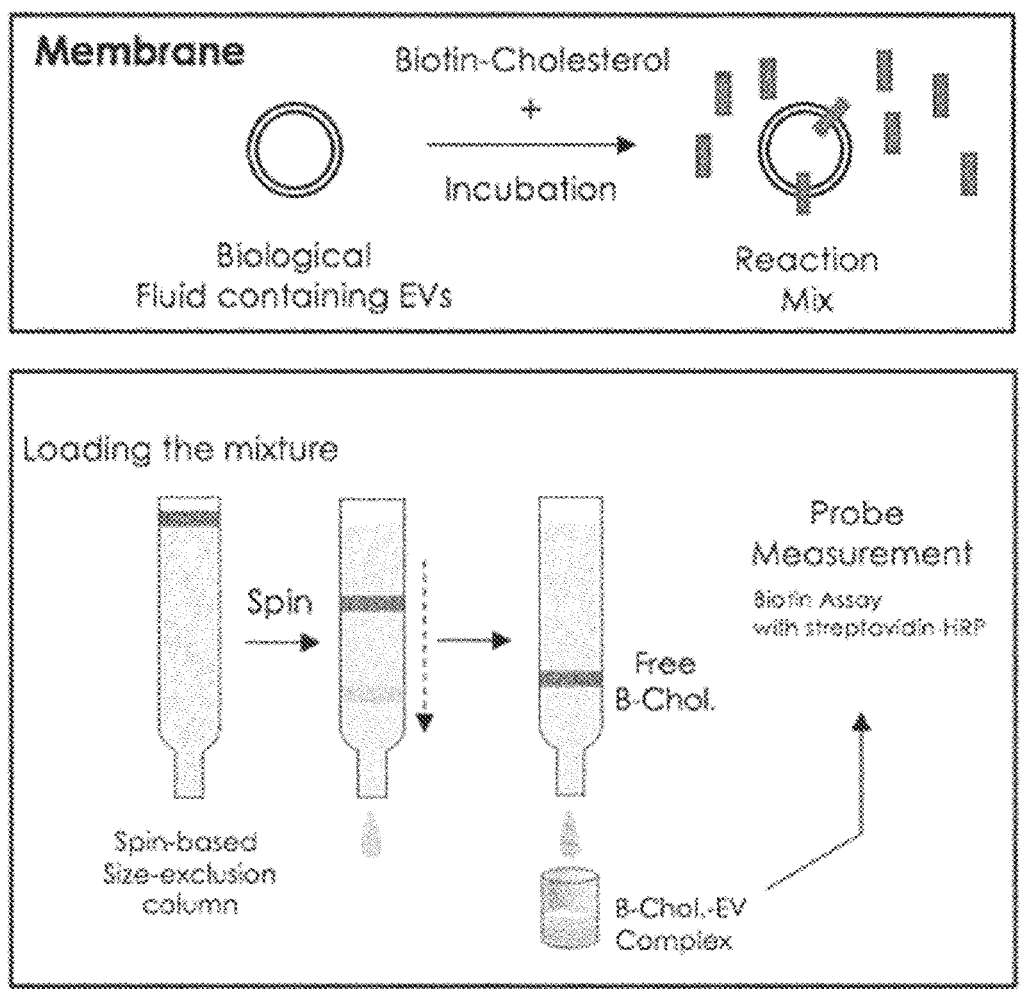
FIG. 18 shows quantitative analysis results of biotin-cholesterol-extracellular vesicle complexes separated by spin-based size-exclusion chromatography of human urine (B) and human plasma (C) incubated with biotin-cholesterol.
Figure 18B:
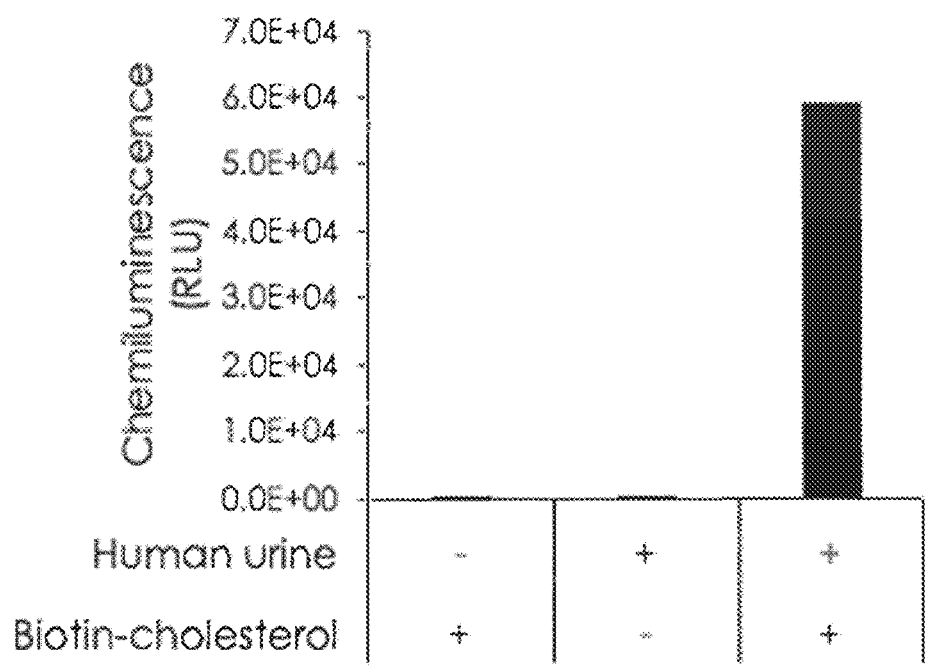
Figure 18C:
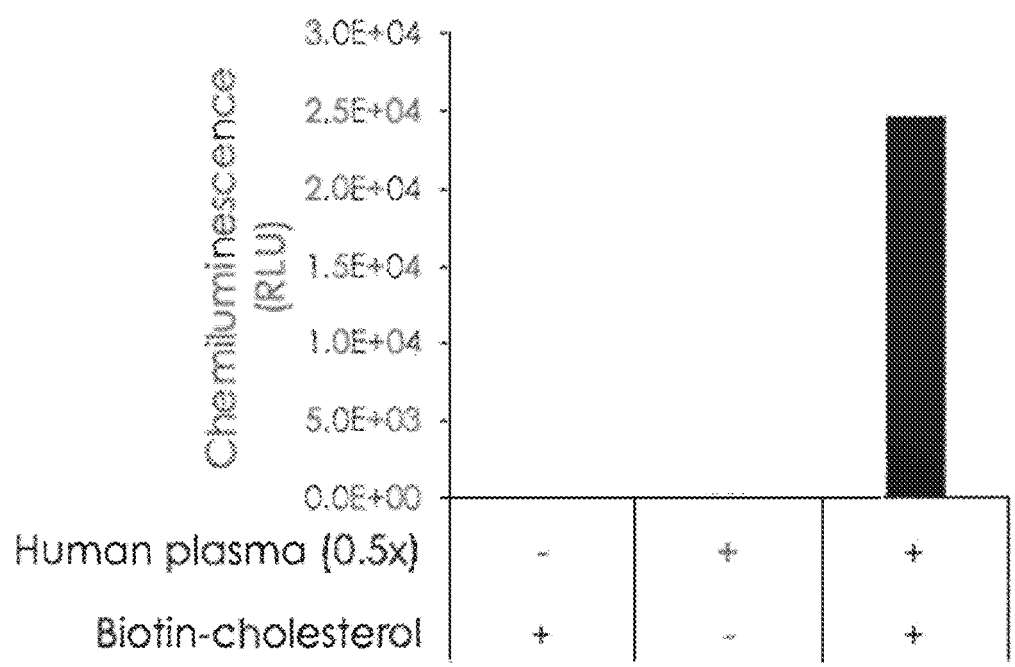

Example 9: Analysis of Extracellular Vesicles in Body Fluid Using Spin-Based Size-Exclusion Chromatography and Cholesterol Probe As confirmed in Example 8, the extracellular vesicles in the cell culture can be analyzed without purification of extracellular vesicles, and the above method was applied to a human body fluid. Specifically, as shown in the schematic diagram of FIG. 18A, human urine or human plasma was mixed with biotin-cholesterol, followed by incubation at 37° C. for 30 min. For the removal of biotin-cholesterol not binding to extracellular vesicles in samples, the mixture solutions were loaded in the spin-based Sephacryl S500 columns, followed by centrifugation at 700×g for 5 min, to thereby harvest eluates. A biotin-cholesterol single group or a biological sample single group as a control was loaded in the column by the same method as above, followed by spinning, to thereby harvest an eluate. To quantify biotin in the eluates, the eluates were placed in 96-well plates (microplates), and then substances in the samples were adsorbed and fixed to the plates. Thereafter, the plates were incubated with streptavidin-peroxidase and washed, and then the chemiluminescence was measured according to the activity of peroxidase remaining on the plates (FIGS. 18B and 18C).

As a result, the chemiluminescence was observed to be very low or absent in the biotin-cholesterol single group and biological sample single group, but a high chemiluminescence was observed in the groups in which biological samples (urine or plasma) and biotin-cholesterol were mixed and incubated. The results showed that biotin-cholesterol molecules were inserted into the lipid bilayer of extracellular vesicles in the biological sample and can be eluted together with extracellular vesicles from the spin-based pretreatment size-exclusion chromatography column, indicating that the above method can be utilized in the measurement of the total amount of extracellular vesicles present in various body fluids.

Example 10: Analysis of Reference Extracellular Vesicles Using Spin-Based Size-Exclusion Chromatography and Lipophilic Probe (Dil)

Figure 19A:
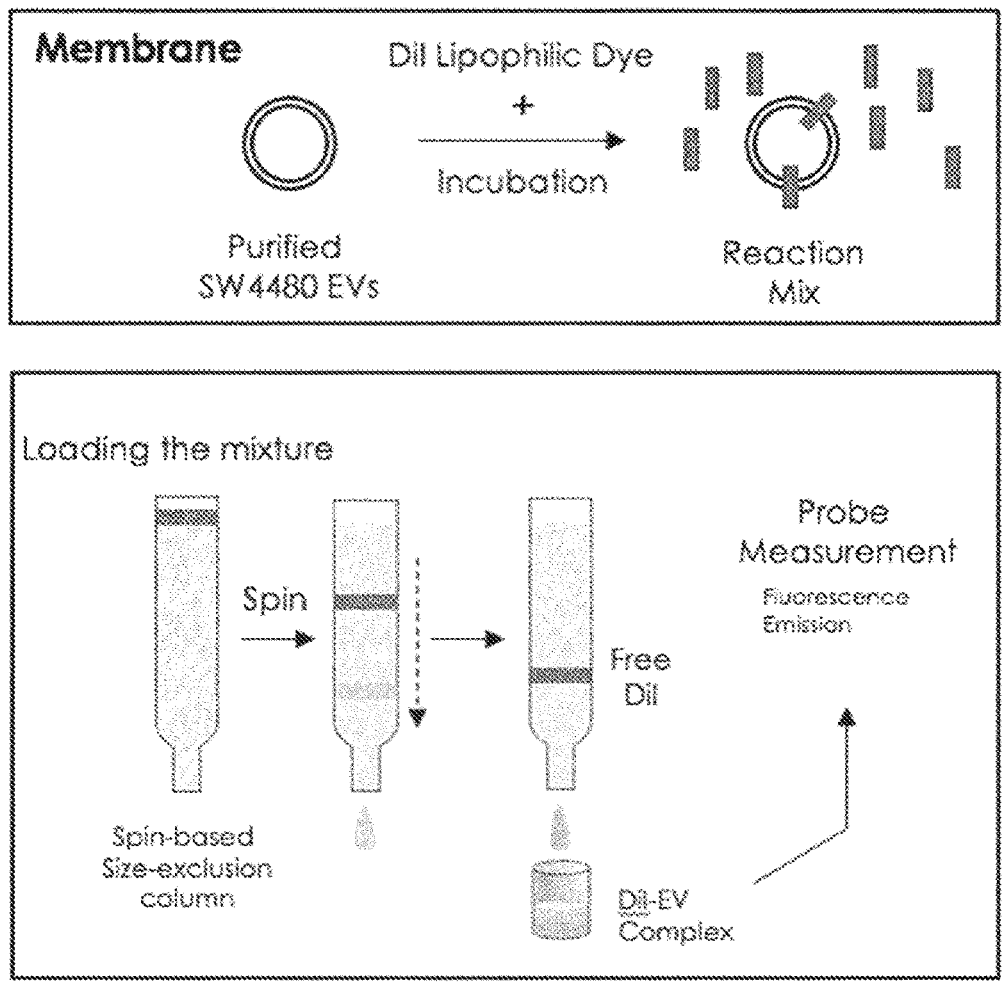
FIG. 19 shows a fluorescence chromatogram obtained by HPLC analysis of reference extracellular vesicles incubated with Dil (lipophilic dye) according to an example of the present invention.
Figure 19B:
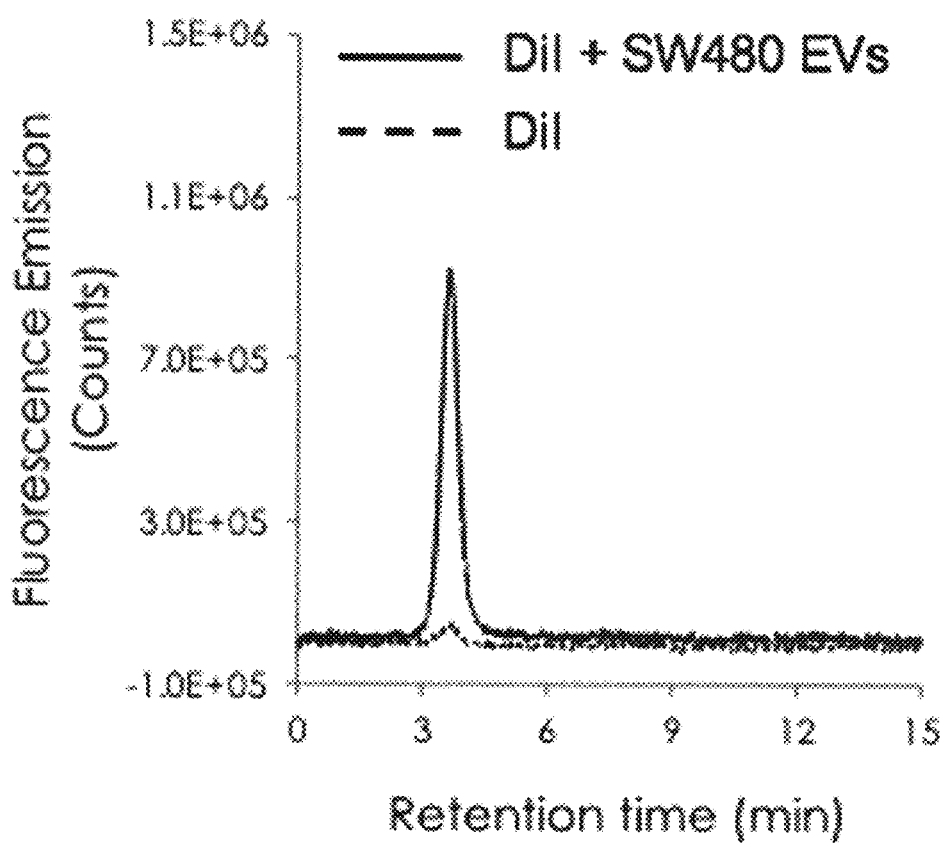

A further test was carried out using fluorescently labeled lipophilic Dil, instead of cholesterol, as a probe binding to or inserted into a lipid bilayer as one of the components of extracellular vesicles. Specifically, as shown in the schematic diagram of FIG. 19A, fluorescently labeled lipophilic Dil single group or a reference extracellular vesicle and fluorescently labeled lipophilic Dil mixed group was incubated at 37° C. for 30 min, and then, for the removal of fluorescently labeled lipophilic Dil not binding to extracellular vesicles, the respective mixture solutions were loaded in the spin-based Sephacryl S500 columns, followed by centrifugation at 700×g for 5 min, to thereby harvest eluates. Thereafter, the eluates were injected into Sephacryl S500 columns and developed using HPLC systems, and the 280 nm-absorption chromatogram and the fluorescence chromatogram (FIG. 19B) were analyzed.

As a result, the small-molecular weight fluorescently labeled lipophilic Dil cannot be eluted from the spin-based size-exclusion chromatography column and thus no fluorescence band was detected, but a high fluorescence band was detected at 3.5 min, which is the time of elution of extracellular vesicles, in the reference extracellular vesicle and fluorescently labeled lipophilic DiI mixed group. The results indicated that the small-molecular weight fluorescently labeled lipophilic DiI is inserted into the lipid bilayer of extracellular vesicles and eluted together with extracellular vesicles from the spin-based size-exclusion chromatography column.

Example 11: Analysis of *E. coli*-Derived Extracellular Vesicles Using Spin-Based Size-Exclusion Chromatography and Lipophilic Probe (DiI)

Figure 20B:
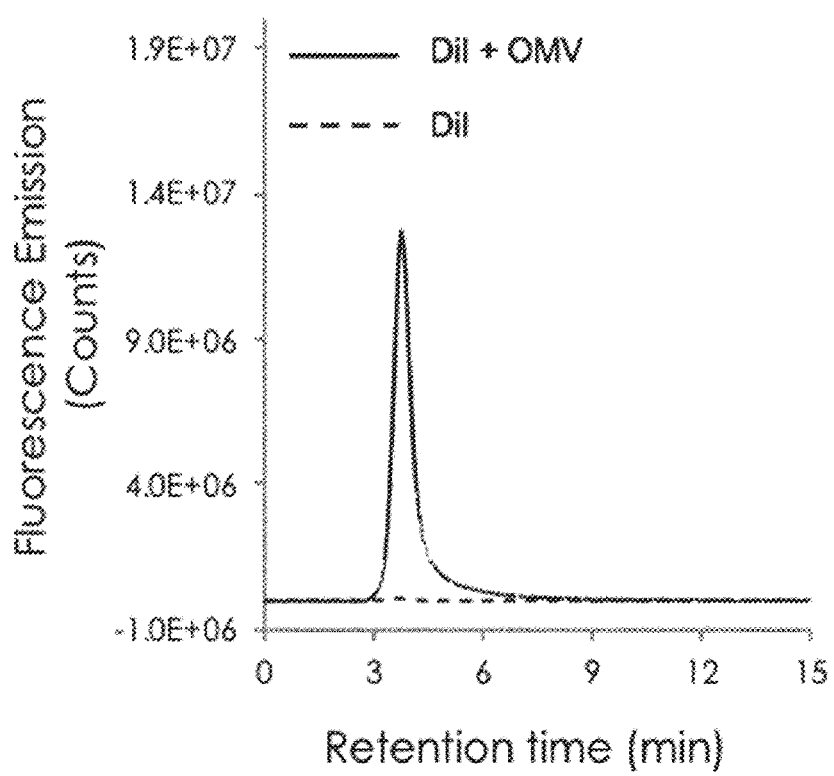
FIG. 20 shows a fluorescence chromatogram obtained by HPLC analysis of *E. coli*-derived extracellular vesicles incubated with Dil (lipophilic dye) according to an example of the present invention.

The analysis was conducted by applying the same probe as in Example 10 to *E. coli*-derived extracellular vesicles. Specifically, as shown in the schematic diagram of FIG. 20A, fluorescently labeled lipophilic DiI single group or an *E. coli*-derived extracellular vesicle and fluorescently labeled lipophilic DiI mixed group was incubated at 37° C. for 30 min, and then, for the removal of fluorescently labeled lipophilic DiI not binding to extracellular vesicles, the respective mixture solutions were loaded in the spin-based Sephacryl S500 columns, followed by centrifugation at 700×g for 5 min, to thereby harvest eluates. Thereafter, the eluates were injected into Sephacryl S500 columns and developed using HPLC systems, and the 280 nm-absorption chromatogram and the fluorescence chromatogram (FIG. 20B) were analyzed.

As a result, the small-molecular weight fluorescently labeled lipophilic DiI cannot be eluted from the spin-based size-exclusion chromatography column and thus no fluorescence band was detected, but a high fluorescence band was detected at 3.5 min, which is the time of elution of extracellular vesicles, in the *E. coli*-derived extracellular vesicle and fluorescently labeled lipophilic DiI mixed group. These results indicated that the small-molecular weight fluorescently labeled lipophilic DiI is inserted into the lipid bilayer of extracellular vesicles and eluted together with extracellular vesicles from the spin-based size-exclusion chromatography column.

Therefore, it was confirmed that the bacteria-derived extracellular vesicles also contain a lipid bilayer and that the present analysis method can be utilized in the analysis of the total amount of extracellular vesicles as well as the characteristics of extracellular vesicles.

The invention claimed is:

1. A method for analysis of extracellular vesicles, the method comprising:
(a) mixing probes and a sample containing extracellular vesicles, followed by reaction, wherein each of the probes contains a binding portion specifically binding to components of the extracellular vesicles, and a detectable signal portion;
(b) injecting the mixed sample through a size-exclusion chromatography column, followed by development; and
(c) detecting extracellular vesicle-probe complexes and free probes from the developed sample, and quantifying the amount of the components of the extracellular vesicles by quantifying the amount of extracellular vesicle-probe complexes and the amount of the free probes.

2. The method of claim 1, wherein each of the probes is a single substance which contains a binding portion specifically binding to the components of the extracellular vesicles, and a detectable signal portion; or a composite substance in which a substance containing at least one analyzable signal portion is bound to a substance containing a binding portion specifically binding to the components of the extracellular vesicles.

3. The method of claim 1, wherein the binding portion of each of the probes specifically binds to at least one component selected from the group consisting of membrane surface components of the extracellular vesicles, membrane components of the extracellular vesicles, and intracellular components of the extracellular vesicles.

4. The method of claim 1, wherein each of the probes is at least one selected from the group consisting of proteins, antibodies, antibody-derived substances, peptides, nucleic acids, nucleic acid-amino acid complexes, enzymes, enzyme substrates, and chemical ligands.

5. The method of claim 1, wherein each of the probes contains at least one signal portion selected from the group consisting of fluorescent substances, enzyme substrates, proteins, peptides, nucleic acids, biotins, metals, and radioisotopes.

6. The method of claim 1, wherein the step of detecting comprises quantifying extracellular vesicles by analyzing an absorption chromatogram at a predetermined wavelength.

7. The method of claim 6, wherein the predetermined wavelength has at least one value selected from a range of 200-800 nm.

8. The method of claim 1, wherein the step of detecting comprises quantifying the probes by detecting the signal portion of the probes.

9. The method of claim 8, wherein the step of detecting of the signal portion of the probe comprises conducting at least one selected from the group consisting of spectroscopic analysis, physicochemical analysis, quantum chemical analysis, enzymatic analysis, biotin analysis, and nucleic acid analysis.

10. The method of claim 1, wherein the sample is at least one selected from the group consisting of mammalian cell culture media, bacterial cell culture media, yeast culture media, tissue extracts, cancer tissues, serum, blood plasma, saliva, tears, aqueous humor, sweat, urine, feces, cerebrospinal fluid (CSF), ascites, amniotic fluid, semen, milk, dust, fresh water, seawater, soil, and fermented foods.

11. A method for analysis of the components of extracellular vesicles, the method comprising:
(a) mixing probes and a sample containing extracellular vesicles, followed by reaction, wherein each of the probes contains a binding portion specifically binding to components of the extracellular vesicles, and a detectable signal portion;
(b) injecting the mixed sample through a spin-based size-exclusion chromatography column, followed by development;
(c) separating extracellular vesicle-probe complexes from the size-exclusion chromatography column; and
(d) detecting the probes from the separated extracellular vesicle-probe complexes,
wherein the binding portion of each probe specifically binds to a particular component of the extracellular vesicles selected from the group consisting of a membrane surface component of the extracellular vesicles, a membrane component of the extracellular vesicles, and an intracellular component of the extracellular vesicles.

12. The method of claim 11, wherein each of the probes is a single substance which contains a binding portion specifically binding to the components of the extracellular vesicles, and a detectable signal portion; or a composite substance in which a substance containing at least one analyzable signal portion is bound to a substance containing a binding portion specifically binding to the components of the extracellular vesicles.

13. The method of claim 11, wherein each of the probes is at least one selected from the group consisting of proteins, antibodies, antibody-derived substances, peptides, nucleic acids, nucleic acid-amino acid complexes, enzymes, enzyme substrates, and chemical ligands.

14. The method of claim 11, wherein each of the probes contains at least one signal portion selected from the group consisting of fluorescent substances, enzyme substrates, enzymes, proteins, peptides, nucleic acids, biotins, metals, and radioisotopes.

15. The method of claim 11, wherein the step of detecting comprises quantifying the extracellular vesicles by analyzing an absorption chromatogram at a predetermined wavelength.

16. The method of claim 15, wherein the predetermined wavelength has at least one value selected from a range of 200-800 nm.

17. The method of claim 11, wherein the step of detecting comprises quantifying the probes by detecting the signal portion of the probes.

18. The method of claim 17, wherein the step of detecting the signal portion of the probes comprises conducting at least one selected from the group consisting of spectroscopic analysis, physicochemical analysis, quantum chemical analysis, enzymatic analysis, biotin analysis, radiation analysis, and nucleic acid analysis.

19. The method of claim 11, wherein the sample is at least one selected from the group consisting of mammalian cell culture media, bacterial cell culture media, yeast culture media, tissue extracts, cancer tissues, serum, blood plasma, saliva, tears, aqueous humor, sweat, urine, feces, cerebrospinal fluid (CSF), ascites, amniotic fluid, semen, milk, dust, fresh water, seawater, soil, and fermented foods.

* * * * *